US011181428B2

(12) United States Patent
Baer et al.

(10) Patent No.: US 11,181,428 B2
(45) Date of Patent: Nov. 23, 2021

(54) SYSTEMS AND METHODS FOR DETECTING RUNNING AND WALKING STRIDES AND FOOT STRIKES

(71) Applicants: Thomas Michael Baer, Mountain View, CA (US); Jonathan William Baer, Mountain View, CA (US)

(72) Inventors: Thomas Michael Baer, Mountain View, CA (US); Jonathan William Baer, Mountain View, CA (US)

(*) Notice: Subject to any disclaimer, the term of this patent is extended or adjusted under 35 U.S.C. 154(b) by 0 days.

(21) Appl. No.: 17/100,322

(22) Filed: Nov. 20, 2020

(65) Prior Publication Data

US 2021/0156754 A1  May 27, 2021

Related U.S. Application Data

(60) Provisional application No. 62/938,742, filed on Nov. 21, 2019.

(51) Int. Cl.
*G01L 1/22* (2006.01)
*A61B 5/11* (2006.01)
(Continued)

(52) U.S. Cl.
CPC .............. *G01L 1/225* (2013.01); *A61B 5/112* (2013.01); *G01L 1/205* (2013.01);
(Continued)

(58) Field of Classification Search
CPC ......... G01L 1/225; G01L 1/205; A61B 5/112; A63B 24/0087; A63B 71/0622;
(Continued)

(56) References Cited

U.S. PATENT DOCUMENTS 4,489,302 A * 12/1984 Eventoff ............. B60C 23/0408
                                                        338/100
4,659,090 A *  4/1987 Kustanovich ........... G01L 1/144
                                                        273/376
(Continued)

FOREIGN PATENT DOCUMENTS

WO    WO-2007107523 A1 *  9/2007  ............... G01L 1/20

OTHER PUBLICATIONS

Phung, Wayne "Electric Stride". UCSD ECE Design Competition 2019. Jun. 2019. <https://waynephung.com/ElectricStride.html> (Year: 2019).*

(Continued)

*Primary Examiner* — Jonathan M Dunlap
(74) *Attorney, Agent, or Firm* — McDonnell Boehnen Hulbert & Berghoff LLP

(57) ABSTRACT

The present disclosure relates to systems and methods for measuring the location, the amplitude, and/or the direction of forces applied to a walking or running surface. An example system includes a pressure-sensitive sheet that extends along a first axis. The pressure-sensitive sheet includes a top surface and a bottom surface. A vertical force applied at a location along at least one of the top surface or the bottom surface forms an electrical path between the top surface and the bottom surface having a resistance, $r_f$, that is inversely proportional to an amplitude of the vertical force. The system further includes read out circuitry configured to provide information indicative of the amplitude of the vertical force and the location of the vertical force along the first axis of the pressure-sensitive sheet.

14 Claims, 17 Drawing Sheets

US 11,181,428 B2
Page 2

(51) Int. Cl.
*G01L 1/20* (2006.01)
*A63B 71/06* (2006.01)
*G09B 19/00* (2006.01)
*A63B 24/00* (2006.01)
*A63B 26/00* (2006.01)
*A63B 22/00* (2006.01)
*A63B 23/04* (2006.01)

(52) U.S. Cl.
CPC ....... *A63B 23/0464* (2013.01); *A63B 24/0087* (2013.01); *A63B 26/003* (2013.01); *A63B 71/0622* (2013.01); *A63B 2022/0092* (2013.01); *A63B 2071/063* (2013.01); *A63B 2071/0625* (2013.01); *A63B 2071/0627* (2013.01); *A63B 2225/20* (2013.01); *A63B 2225/50* (2013.01); *A63B 2225/74* (2020.08); *G09B 19/0038* (2013.01)

(58) Field of Classification Search
CPC .............. A63B 26/003; A63B 23/0464; A63B 2225/74; A63B 2225/50; A63B 2225/20; A63B 2022/0092; A63B 2071/0627; A63B 2071/063; A63B 2071/0625; G09B 19/0038
See application file for complete search history.

(56) References Cited

U.S. PATENT DOCUMENTS

| | | | | |
|---|---|---|---|---|
| 5,013,958 A * | 5/1991 | Ohnishi | ................ | H02N 2/028 310/323.16 |
| 5,060,527 A * | 10/1991 | Burgess | ................ | G06F 3/045 73/862.68 |
| 5,180,230 A * | 1/1993 | McCarthy | ............... | F16C 29/04 384/54 |
| 5,847,639 A * | 12/1998 | Yaniger | ................ | G01L 1/20 338/99 |
| 6,119,530 A * | 9/2000 | Oddsson | ................ | A61B 5/00 73/862.42 |
| 7,174,793 B2 * | 2/2007 | Morimoto | ............... | G01L 1/146 73/862.045 |
| 10,413,230 B1 | 9/2019 | Berme et al. | | |
| 10,503,306 B2 * | 12/2019 | Yi | ............ | G01L 1/205 |
| 10,506,967 B2 * | 12/2019 | Guo | ....................... | G01G 19/50 |
| 10,704,965 B2 * | 7/2020 | Haick | ........ | G01L 1/16 |
| 2004/0055396 A1 * | 3/2004 | Morimoto | ............... | G01L 1/205 73/862.045 |
| 2004/0259690 A1 | 12/2004 | Frykman et al. | | |
| 2005/0022615 A1 | 2/2005 | Fortune et al. | | |
| 2005/0072249 A1 * | 4/2005 | Maeda | ................... | B60N 2/002 73/862.046 |
| 2008/0271933 A1 * | 11/2008 | Morimoto | ............... | A61B 5/447 178/18.05 |
| 2009/0134966 A1 | 5/2009 | Baker | | |
| 2010/0117993 A1 | 5/2010 | Kent | | |
| 2010/0242629 A1 * | 9/2010 | Leuenberger | ......... | A61J 7/0418 73/862.625 |
| 2016/0166876 A1 * | 6/2016 | Goh | ................... | A63B 21/4037 482/9 |
| 2016/0296801 A1 * | 10/2016 | De La Garza | ..... | A63B 71/0622 |
| 2017/0197032 A1 | 7/2017 | Demas et al. | | |
| 2017/0363489 A1 * | 12/2017 | Haick | ....................... | G01L 1/16 |
| 2018/0095580 A1 * | 4/2018 | Yi | ............ | G01L 1/205 |
| 2018/0184966 A1 * | 7/2018 | Guo | .......................... | G01L 5/00 |
| 2018/0345068 A1 | 12/2018 | Beyer et al. | | |
| 2020/0222777 A1 * | 7/2020 | Zimmerman | ............. | E06C 1/56 |

OTHER PUBLICATIONS

International Searching Authority, International Search Report and Written Opinion dated Feb. 10, 2021, issued in connection with International Patent Application No. PCT/US2020/061560 filed on Nov. 20, 2020, 11 pages.

\* cited by examiner

SYSTEMS AND METHODS FOR DETECTING RUNNING AND WALKING STRIDES AND FOOT STRIKES

CROSS-REFERENCE TO RELATED APPLICATION

The present application claims the benefit of U.S. Provisional Patent Application No. 62/938,742, filed Nov. 21, 2019, the content of which is herewith incorporated by reference.

BACKGROUND

Gait analysis is the study of animal locomotion, more specifically the study of human motion, conventionally based on observations of viewers. By studying a person's gait, physical therapists and doctors may be more able to assess and treat individuals with conditions affecting their ability to walk. Gait analysis is used in sports biomechanics to help athletes run more efficiently and to identify posture-related or movement-related problems in people with injuries.

In some conventional applications, gait analysis may be augmented by instrumentation for measuring body movements, body mechanics, and the activity of the muscles. For example, an individual may walk or run on a treadmill while being imaged by one or more cameras to measure stride length and/or other gait characteristics.

However, there exists a need for more effective systems and methods to characterize gait and other types of athletic movements and motion.

SUMMARY

The present disclosure generally relates to systems and methods for measure of the forces during various physical movements such as: running, walking, jumping, lateral change of direction, etc., and the timing and positions of an individual's feet during such movements.

In a first aspect, a vertical force transducer system is provided. The vertical force transducer system includes a pressure-sensitive sheet that extends along a first axis. The pressure-sensitive sheet includes a top surface and a bottom surface. A vertical force applied at a location along at least one of the top surface or the bottom surface forms an electrical path between the top surface and the bottom surface having a resistance, $r_f$, that is inversely proportional to an amplitude of the vertical force. The vertical force transducer system also includes read out circuitry configured to provide information indicative of the amplitude of the vertical force and the location of the vertical force along the first axis of the pressure-sensitive sheet. The read out circuitry includes a top electrode extending along the top surface of the pressure-sensitive sheet, a bottom electrode extending along the bottom surface of the pressure-sensitive sheet, and a voltage source configured to provide a reference voltage, $V_0$, with respect to at least one of the top electrode or the bottom electrode.

In a second aspect, a lateral force transducer system is provided. The lateral force transducer system includes a base plate, a top plate slidably coupled to the base plate, and a plurality of friction-reducing elements disposed between the base plate and the top plate. The lateral force transducer system also includes at least two restraining brackets disposed proximate to opposite sides of the base plate. The restraining brackets are configured to restrict lateral movement of the top plate with respect to the base plate. The lateral force transducer system additionally includes a force sensor coupled to each restraining bracket. Each force sensor is configured to measure a lateral force applied to the top plate and transferred to a given restraining bracket. The lateral force transducer system yet further includes read out circuitry configured to provide information indicative of an amplitude of the lateral force and a direction of the lateral force.

In a third aspect, a vertical and lateral force transducer system is provided. The vertical and lateral force transducer system includes a base plate and a top plate slidably coupled to the base plate. The top plate includes a pressure-sensitive sheet that extends along a first axis. The pressure-sensitive sheet includes a top surface and a bottom surface. A vertical force applied at a location along at least one of the top surface or the bottom surface forms an electrical path between the top surface and the bottom surface having a resistance, $r_f$, that is inversely proportional to an amplitude of the vertical force. The vertical and lateral force transducer system also includes a plurality of friction-reducing elements disposed between the base plate and the top plate. The vertical and lateral force transducer system yet further includes at least two restraining brackets disposed proximate to opposite sides of the base plate. The restraining brackets are configured to restrict lateral movement of the top plate with respect to the base plate. The vertical and lateral force transducer system yet further includes a force sensor coupled to each restraining bracket. Each force sensor is configured to measure a lateral force applied to a given restraining bracket. The vertical and lateral force transducer system additionally includes read out circuitry. The read out circuitry includes a top electrode extending along the top surface of the pressure-sensitive sheet and a bottom electrode extending along the bottom surface of the pressure-sensitive sheet. The read out circuitry further includes a voltage source configured to provide a reference voltage, $V_0$, between the top electrode and the bottom electrode. The read out circuitry is configured to provide information indicative of: the amplitude of the vertical force, the location of the vertical force, the amplitude of the lateral force, and a direction of the lateral force.

In a fourth aspect, a method is provided. The method includes receiving, from read out circuitry of a vertical force transducer system, information indicative of a vertical force applied to a pressure-sensitive sheet. The method also includes determining, based on the received information, an amplitude of the vertical force and determining, based on the received information, a location of the vertical force along a first axis of the pressure-sensitive sheet.

In a fifth aspect, a method is provided. The method includes receiving, from read out circuitry of a lateral force transducer system, information indicative of a lateral force applied to a top plate. The method yet further includes determining, based on the received information, an amplitude of the lateral force and determining, based on the received information, a direction of the lateral force.

In a sixth aspect, a method is provided. The method includes receiving, from read out circuitry of a vertical and lateral force transducer system, information indicative of a vertical force and a lateral force applied to a top plate. The method additionally includes determining, based on the received information, an amplitude of the vertical force. The method yet further includes determining, based on the received information, a location of the vertical force along a first axis of a pressure-sensitive sheet. The method also includes determining, based on the received information, an amplitude of the lateral force, and determining, based on the received information, a direction of the lateral force.

Other aspects, embodiments, and implementations will become apparent to those of ordinary skill in the art by reading the following detailed description, with reference where appropriate to the accompanying drawings.

DETAILED DESCRIPTION

Figure 1A:
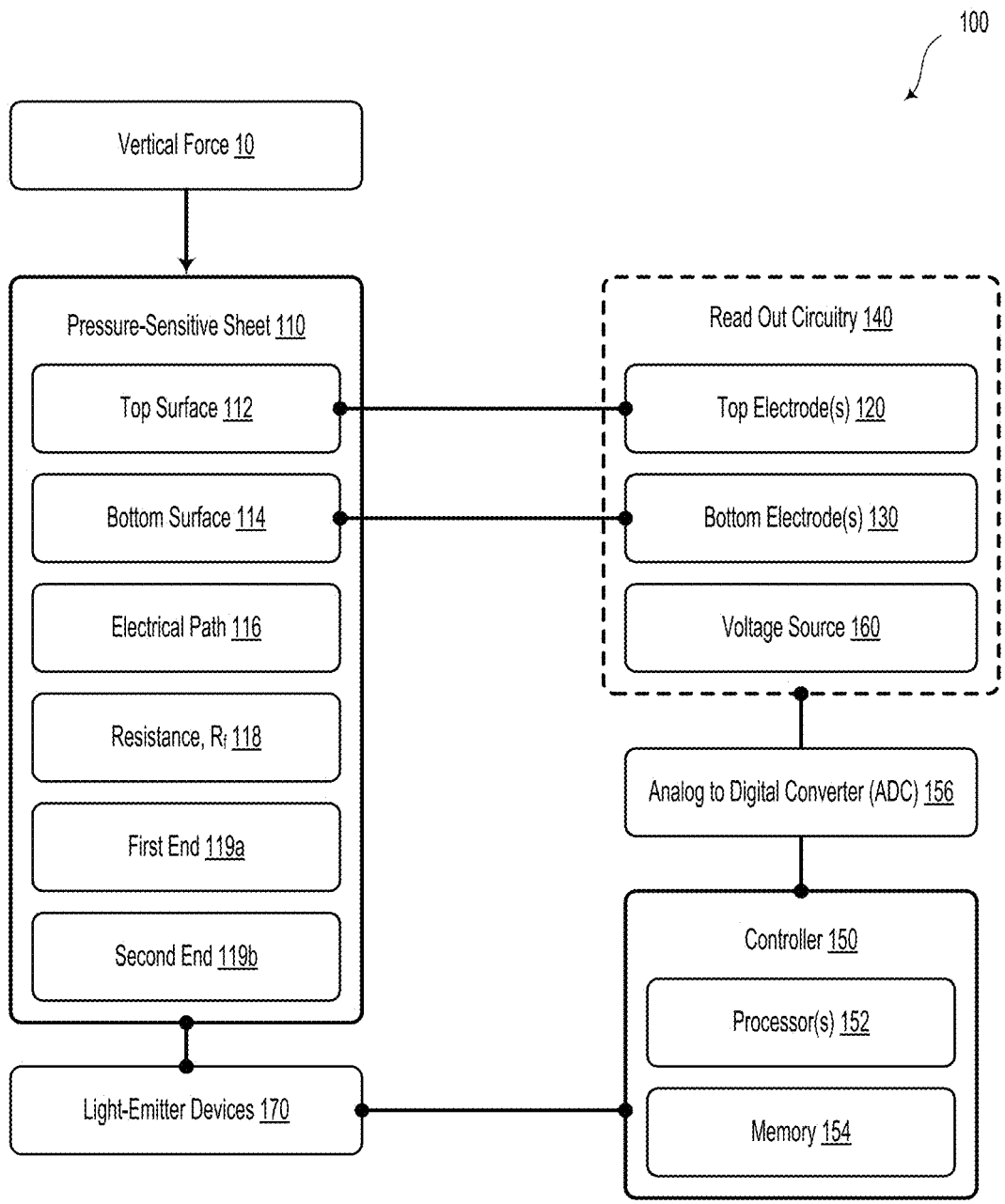
FIG. 1A illustrates a vertical force transducer system, according to an example embodiment.

Example methods, devices, and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Other embodiments can be utilized, and other changes can be made, without departing from the scope of the subject matter presented herein.

Thus, the example embodiments described herein are not meant to be limiting. Aspects of the present disclosure, as generally described herein, and illustrated in the figures, can be arranged, substituted, combined, separated, and designed in a wide variety of different configurations, all of which are contemplated herein.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

I. Overview

Examples described herein include systems and methods for measure the forces during various physical movements such as: running, walking, jumping, lateral change of direction, etc., and the timing and positions of an individual's feet during such movements. Measurements of these forces and the locations of where such forces are applied can be used to characterize athletic performance, track recovery from injury, and help determine appropriate footwear, among many other applications. The measurements described herein can be analyzed (e.g., with a computing device) to provide important diagnostic information to athletes, athletic trainers, doctors, and patients.

An example system may include a plurality of force sensors, which may utilize force-sensing resistors. In such scenarios, the resistance of the force-sensing resistors varies with applied transverse (normal) force. Such force sensors can be disposed both in discrete and extended geometries to provide force and distance measurements. Other embodiments may additionally or alternatively include other types of force-sensing devices such as piezo electric devices and/or load cells.

When walking, running, or jumping, forces are applied through the feet of the person moving to the ground surface in both the vertical and horizontal (e.g., lateral) directions. Vertical force measurements can provide information on how the foot impacts the ground and the efficiency of this force transfer. Vertical forces can be transferred from the ground through the leg of a runner and can cause impact injuries if the ground/foot vertical contact is excessive. The horizontal or lateral forces can provide a measure of strength and acceleration, and the speed and timing of a change in direction.

The systems and methods described herein to characterize foot impact positions and timing can beneficially provide independent measures of velocity and acceleration and can be used to determine how these parameters vary with distance. This information can be utilized to more effectively measure field and track performance, as well as performance in other sports, such as football, soccer, basketball, hockey, and baseball.

II. Example Devices and Systems

A. Vertical Force Transducer System

FIG. 1A illustrates a vertical force transducer system 100, according to an example embodiment. The vertical force transducer system 100 includes a pressure-sensitive sheet 110 that extends along a first axis (e.g., along or parallel to a walking and/or running surface or another type of surface). The pressure-sensitive sheet 110 includes a top surface 112 and a bottom surface 114. An applied force (e.g., a vertical force 10 or force normal to the pressure-sensitive sheet 110) applied at a location along at least one of the top surface 112 or the bottom surface 114 forms an electrical path 116 between the top surface 112 and the bottom surface 114 having a resistance 118, $r_f$, that is inversely proportional to an amplitude of the vertical force 10.

The vertical force transducer system 100 additionally includes read out circuitry 140. The read out circuitry 140 is configured to provide information indicative of the amplitude of the vertical force 10 and the location of the vertical force 10 along the first axis of the pressure-sensitive sheet 110.

The read out circuitry 140 includes a top electrode 120 that extends along the top surface 112 of the pressure-sensitive sheet 110. The read out circuitry 140 additionally includes a bottom electrode 130 that extends along the bottom surface 114 of the pressure-sensitive sheet 110. The read out circuitry 140 also includes a voltage source 160 configured to provide a reference voltage, $V_0$, between 1) one of: the top electrode 120 or the bottom electrode 130; and 2) a ground reference.

In some embodiments, the pressure-sensitive sheet 110 could have a rectangular shape with a length:width ratio of at least 5:1. Other length:width ratios are possible (e.g., 1:1, 2:1, 10:1, 200:1, etc.) and contemplated within the scope of the present disclosure. In some embodiments, the pressure-sensitive sheet 110 could be a continuous sheet of pressure sensitive material. In other embodiments, the pressure-sensitive sheet 110 could include a plurality of segments of pressure-sensitive material. In yet another embodiment, the pressure-sensitive sheet 110 and/or other elements of the vertical force transducer system 100 could be overlaid and/or integrated into a walking (e.g., a walking path) or running surface (e.g., a running lane or running track).

In some embodiments, at least one of the top electrode 120 or the bottom electrode 114 could have a total resistance, $r_0$, that is equally distributed along the first axis of the pressure-sensitive sheet 110. In other words, the top electrode 120 or the bottom electrode 114 could be selected so as to have a finite resistance (e.g., 10 ohms, 100 ohms, or 1000 ohms, or the like). In such scenarios, a resistance measurement along the length of the top electrode 120 or the bottom electrode 114 may provide a two-point resistance value that increases approximately linearly with a distance between the two probe points placed along the respective electrode. For example, if the top electrode 112 has a total resistance, $r_0$ equal to ten ohms, a two-point probe measurement of about half of the length of the top electrode 120 may indicate approximately five ohms.

In various embodiments, the top electrode 120 or the bottom electrode 130 could be a high conductivity electrode. For example, the top electrode 120 or the bottom electrode 130 could have a resistance of approximately zero ohms (e.g., 0.01 ohms, 0.1 ohms, 1 ohms, or the like). In some embodiments, the high conductivity electrode could be formed from copper and/or another high conductivity, low resistance material.

In example embodiments, it will be understood that a first electrode of the set of electrodes including the top electrode 120 and the bottom electrode 130 could have a finite total resistance $r_0$, while a second electrode (e.g., the opposite electrode) could be a high conductivity electrode. In other words, while the first electrode may have a finite resistance, the second electrode may be configured to have effectively zero resistance.

In some examples, the vertical force transducer system 100 also includes a controller 150. In some embodiments, the controller 150 could include at least one of a field-programmable gate array (FPGA) or an application-specific integrated circuit (ASIC). Additionally or alternatively, the controller 150 may include one or more processors 152 and a memory 154. The one or more processors 152 may include a general-purpose processor or a special-purpose processor (e.g., digital signal processors, etc.). The one or more processors 152 may be configured to execute computer-readable program instructions that are stored in the memory 154. As such, the one or more processors 152 may execute the program instructions to provide at least some of the functionality and operations described herein.

The memory 154 may include or take the form of one or more computer-readable storage media that may be read or accessed by the one or more processors 152. The one or more computer-readable storage media can include volatile and/or non-volatile storage components, such as optical, magnetic, organic or other memory or disc storage, which may be integrated in whole or in part with at least one of the one or more processors 152. In some embodiments, the memory 154 may be implemented using a single physical device (e.g., one optical, magnetic, organic or other memory or disc storage unit), while in other embodiments, the memory 154 can be implemented using two or more physical devices.

As noted, the memory 154 may include computer-readable program instructions that relate to operations of vertical force transducer system 100. As such, the memory 154 may include program instructions to perform or facilitate some or all of the functionality described herein. The controller 150 is configured to carry out operations. In some embodiments, controller 150 may carry out the operations by way of the processor 152 executing instructions stored in the memory 154.

In some embodiments, the operations could include operating various elements of vertical force transducer system 100 to obtain information about the amplitude and/or the location of the vertical force 10. The controller 150 could be configured to carry out other operations as well.

In example embodiments, the operations could include causing the voltage source 160 to provide the reference voltage, $V_0$, between 1) one of: the top electrode 120 or the bottom electrode 130; and 2) a ground reference.

The operations include receiving, from the read out circuitry 140, information indicative of the vertical force 10 applied to the pressure-sensitive sheet 110. The information could include, for example, one or more analog or digital signals based on the vertical force 10.

In various embodiments, the voltages used to calculate the vertical force 10 (inversely proportional to $R_f$) and the location of the applied force (x/d), can be measured using a fast analog to digital converter (ADC) 156 and a digital computer. An example of a suitable A/D device is a Measurement Computing A/D model USB-202. Such devices are capable of performing approximately 100,000 A/D conversions per second, which may beneficially provide sufficient time resolution to accurately record the vertical forces applied to the pressure-sensitive sheet. As an example, an applied vertical force of a walking or running step may have a rise time of a few milliseconds. A suitable ADC may be capable of digitizing several different voltages (e.g., 8 different voltages), which can be used to monitor the voltage at each end (e.g. proximate and distal ends) of both the left and right foot force sensors. A suitable computer is manufactured by Dell Corporation Model XPS 15 with a high speed USB 2.0 interface, which could be configured to accept the high speed data from the ADC.

The operations include determining, based on the received information, an amplitude of the vertical force 10. In some embodiments, determining the amplitude of the vertical force 10 could include calculating an estimated normal force (e.g., 1 Newtons (N), 10 N, 100 N) that is being applied to the pressure-sensitive sheet. As described herein, calculating the estimated normal force could be performed by monitoring voltages at a plurality of voltage nodes in the vertical force transducer system.

The operations additionally include determining, based on the received information, a location, x, of the vertical force 10 along the first axis of the pressure-sensitive sheet 110. In some embodiments, determining the location, x, of the vertical force 10 along the first axis of the pressure-sensitive sheet 110 could include calculating the location, x, based on voltage values measured at each end of the top electrode 120.

Figure 1B:
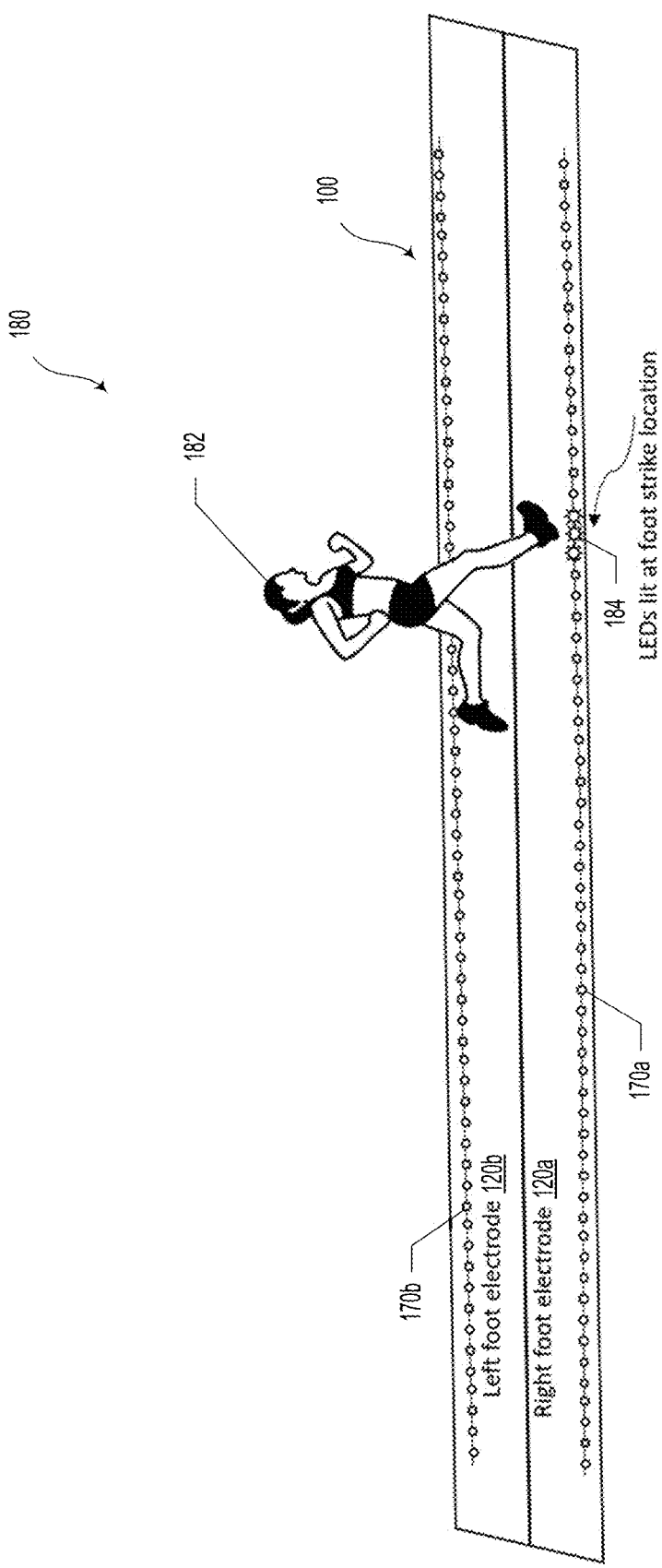
FIG. 1B illustrates a scenario involving a vertical force transducer system, according to an example embodiment.

FIG. 1B illustrates a scenario 180 involving the vertical force transducer system 100, according to an example embodiment. Scenario 180 includes an individual 182 who may walk or run along the vertical force transducer system 100. In such an example, the individual 182 may walk or run along the vertical force transducer system 100 so that the individual's left foot contacts the left foot electrode 120b and the individual's right foot contacts the right foot electrode 120a in an alternate, successive fashion. In some examples, the individual 182 may jump, skip, hop, dance or make other movements along the vertical force transducer system 100.

In an example embodiment, a plurality of light-emitter devices 170a and 170b could be disposed along the sides of the right foot electrode 120a and left foot electrode 120b, respectively. In some examples, the light-emitter devices 170a and 170b could include light-emitting diodes (LEDs), organic LEDs (OLEDs), or the equivalent. In such scenarios, the plurality of light-emitter devices could include periodically-spaced LEDs (e.g., one LED per inch). Additionally or alternatively, light-emitter devices 170a and 170b could include a one-dimensional or two-dimensional array of LEDs, among other possibilities.

In some embodiments, the light-emitter devices could be configured to illuminate in response to at least one of: sensing at least one footfall or a predetermined illumination pattern. For example, light-emitter devices 170a and 170b could be configured to illuminate at locations proximate to foot strikes (e.g., foot strike location 184). Additionally or alternatively, light-emitter devices 170a and 170b could be configured to illuminate based on a predetermined illumination pattern. Such predetermined illumination patterns could include, for example, a "chase" sequence where the individual 182 is challenged to walk or run to keep up with successively-illuminated footfall/stride locations along the length of the vertical force transducer system 100. In some examples, the various locations could be illuminated so that the individual 182 could "race themselves" and/or "race a celebrity" (e.g., a world-champion sprinter or long-distance runner, etc.). Additionally or alternatively, a training mode could provide illuminated footfall locations in an effort to improve athletic performance and/or running/walking form (e.g., speed interval training, triple jump, stride lengthening exercises, etc.). In other embodiments, the light-emitter devices 170a and/or 170b could be configured to fast-blink or slow-blink to indicate a running or walking pace and/or whether the individual 182 should speed up or slow down their walking or running pace. In yet further embodiments, the light-emitter devices 170a and 170b could be illuminated with varying colors to indicate various actions for the individual 182 to take (e.g., green to indicate run, yellow to indicate jog, red to indicate stop, etc.).

Other activities and/or games could be possible within the scope of the present disclosure. For example, users may participate in a game of "hopscotch", which may include a predetermined hop/jump step pattern. Additionally or alternatively, a game of "tag" could include one or more blinking light-emitter devices the individual must "touch" within a time goal. Athletic performance metrics, such as a shuttle run, long jump, 40 yard dash, triple jump, and/or other athletic movements could be indicated by utilizing the light-emitter devices 170a and 170b and could be measured by way of the vertical force transducer system 100 as described herein. In such scenarios, systems and methods described herein could provide spatio-temporal force measurements of physical performance that are more accurate than conventional measurement methods (e.g., stopwatch, pressure-pad, light-beam sensors, etc.). Furthermore, the present systems and methods could provide a valuable athletic training tool to improve athletic performance and individual physical fitness.

Figure 2A:
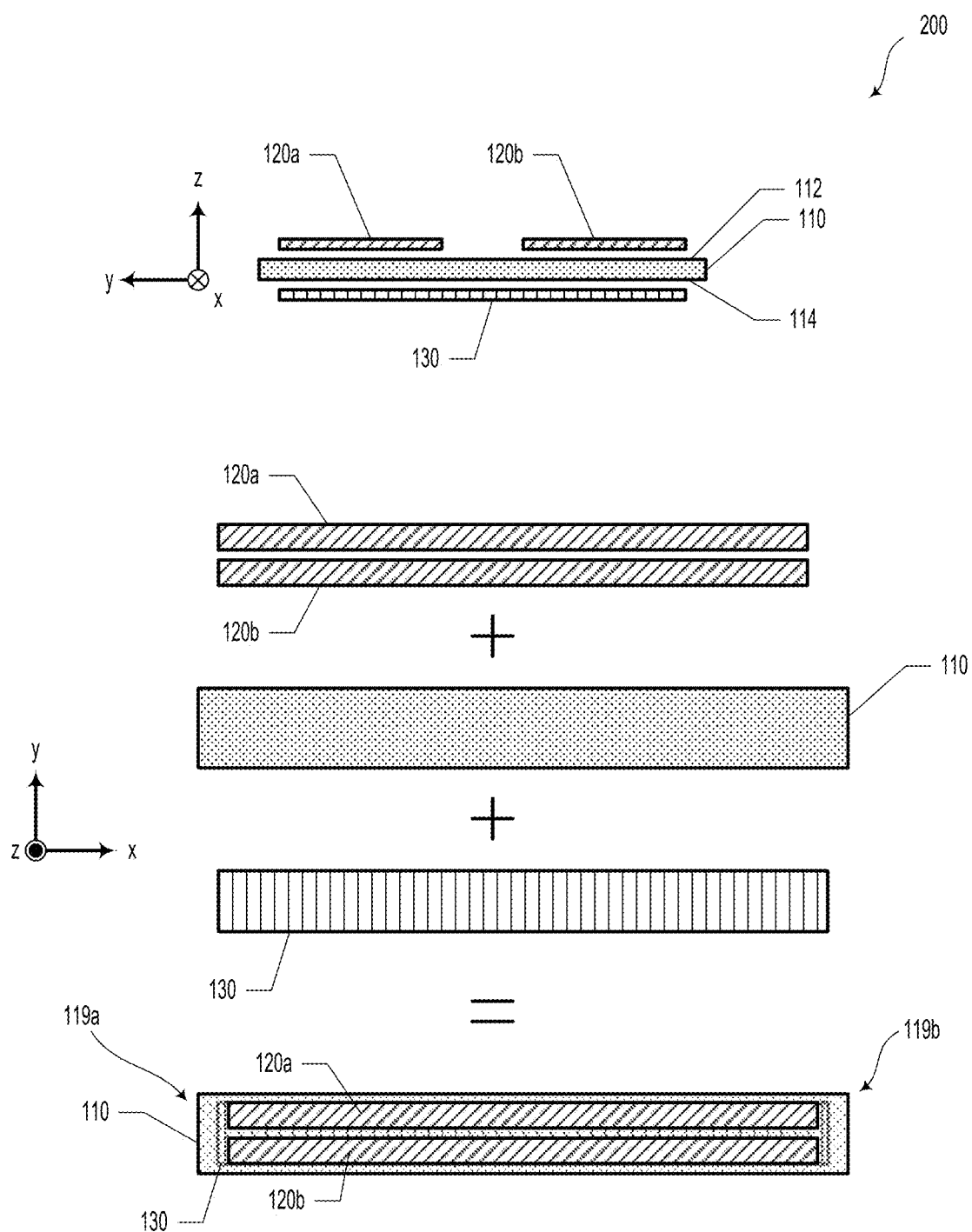
FIG. 2A illustrates a vertical force transducer system, according to an example embodiment.
Figure 2B:
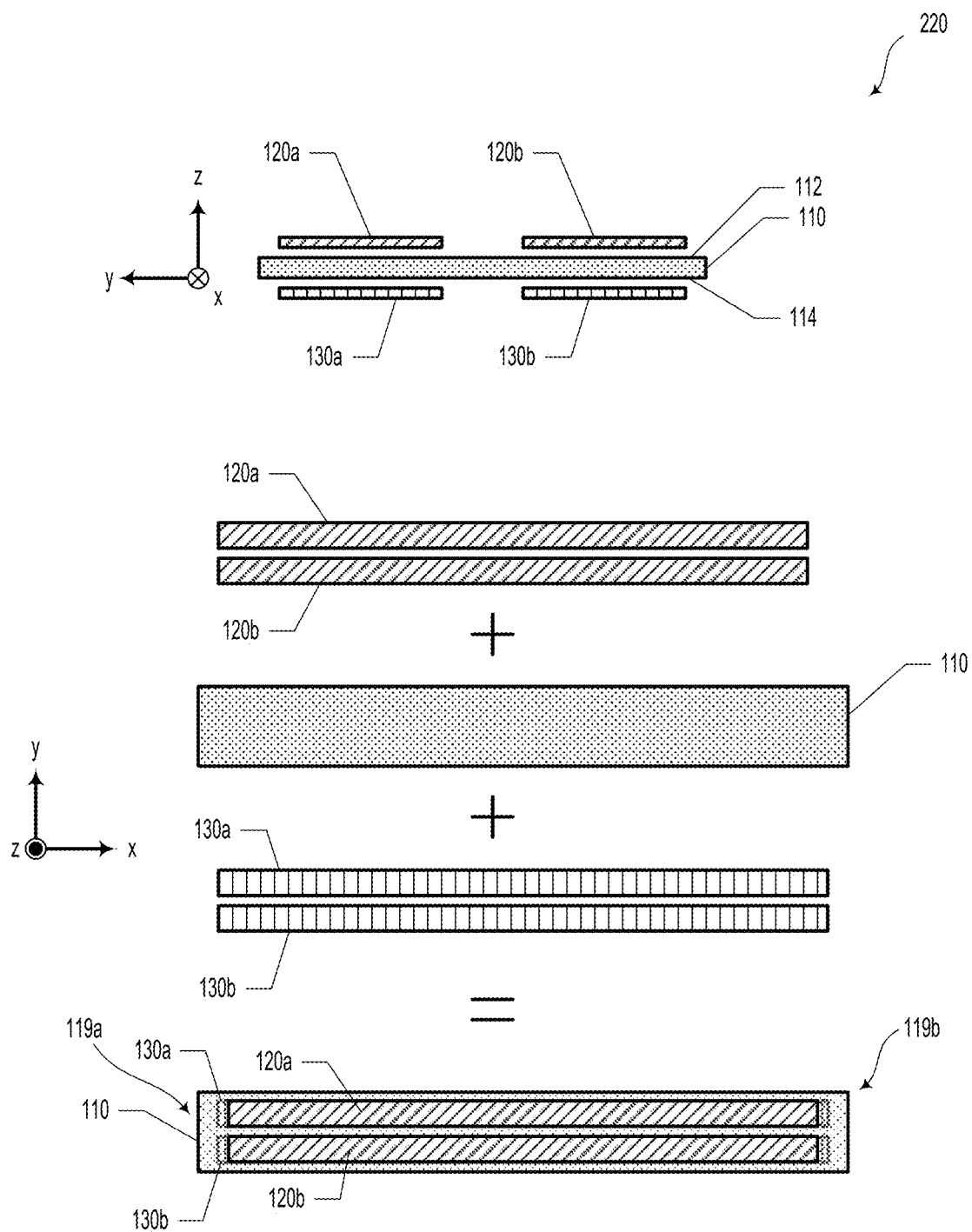
FIG. 2B illustrates a vertical force transducer system, according to an example embodiment.

FIGS. 2A and 2B illustrate respective vertical force transducer systems 200 and 220, according to example embodiments. The vertical force transducer system 200 and/or vertical force transducer system 220 could be similar or identical to vertical force transducer system 100, as illustrated and described in reference to FIGS. 1A and 1B.

While the top electrode 120 and the bottom electrode 130 are described in the singular form in various embodiments described herein, it will be understood that the top electrode 120 and/or the bottom electrode 130 could include a plurality of respective electrodes. As an example, the top electrode 120 could include a right top electrode 120a and a left top electrode 120b, as illustrated and described in reference to FIGS. 2A and 2B. Additionally or alternatively, the bottom electrode 130 could include a right bottom electrode 130a and a left bottom electrode 130b as illustrated and described in reference to FIG. 2B. In yet other embodiments, the top electrode 120 and/or the bottom electrode 130 could include more respective electrodes, such as a plurality of five, ten, twenty, or more electrodes.

Figure 3:
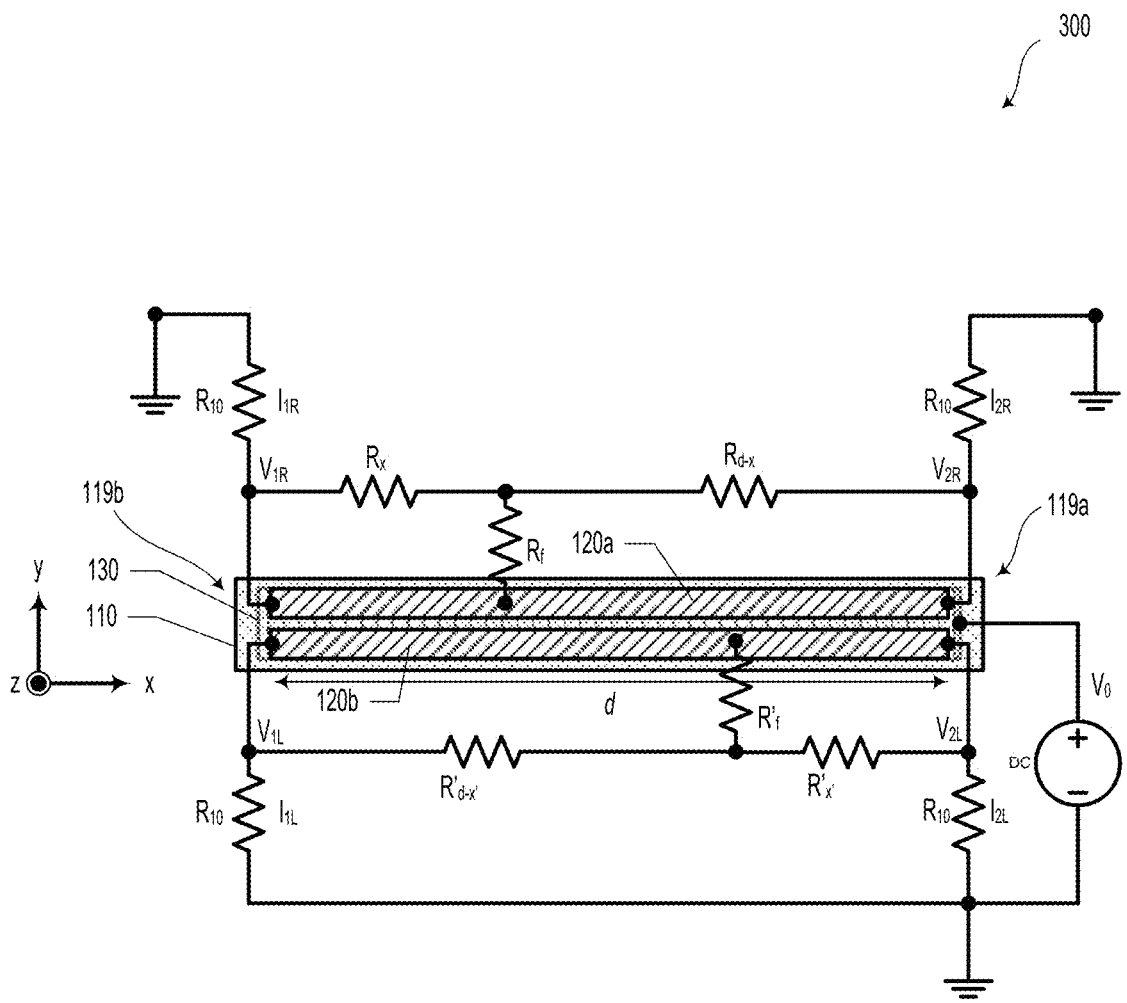
FIG. 3 illustrates a vertical force transducer system, according to an example embodiment.
Figure 3:
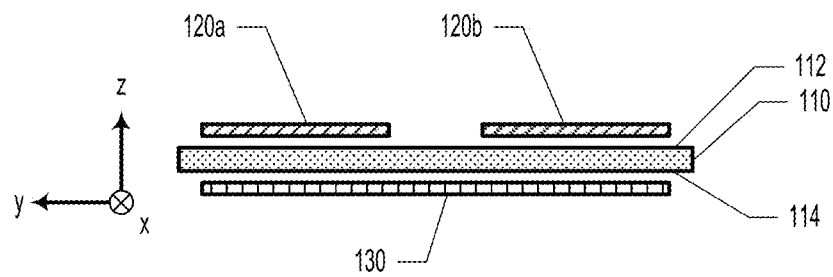

FIG. 3 illustrates a vertical force transducer system 300, according to an example embodiment. Vertical force transducer system 300 could be similar or identical to vertical force transducer systems 100, 200, and 220 as illustrated and described in reference to FIGS. 1A, 1B, 2A, and 2B.

The vertical force transducer system 300 could be operable to quantify vertical forces and foot impact location using a force-sensitive resistor fabricated as a thin sheet of plastic film. An example of such a film is 8 mil thick Velostat, manufactured by 3M. Other types of electrically conductive films and/or packaging materials made of a polymeric foil (polyolefins) and impregnated with carbon black are possible and contemplated. These types of films can be purchased in rolls of many hundreds of feet in length and widths of several feet. The resistance of this film at any point is quite high (e.g., 1,000 ohms, 1,000,000 ohms, or higher) until a vertical force is applied at a specific location. The resistance at this location is then approximately inversely proportional to the applied force. A long running or walking path can be constructed by laying out a length of the pressure-sensitive film sandwiched between top and bottom electrodes extending along the length of the pressure-sensitive film. The resistance between the electrodes will be high until a force is applied to the electrode/film assembly at a specific point. The resistance will then be inversely proportional to the applied force. Current will flow between the electrodes primarily at the point where the force is applied. If one of the electrodes, for example the top electrode, is designed to have a finite resistance that varies with its length, then the position of the impact point and the applied force can be determined by measuring the current flow or voltages at both ends of the running path. The other electrode, for example the bottom electrode, could be designed to have a total low resistance. In such scenarios, the voltage applied to this bottom electrode is constant along its length. It will be understood that the function and/or characteristics of the top electrode and the bottom electrode could be swapped as described herein.

This arrangement allows the measurement of vertical forces caused by stepping on the pressure-sensitive film as well as the location of the foot strike. Vertical force profiles can be used to measure the type of footfall (such as a heel strike versus a toe strike), the impact or rise time of the force versus time, the asymmetry of the force profiles due to injury, the length and timing of the stride, and other variables. As described herein, separate top electrodes can be used to measure left and right foot forces by including a first (left) electrode proximate to left foot strikes and a second (right) electrode proximate to right foot strikes.

Figure 4:
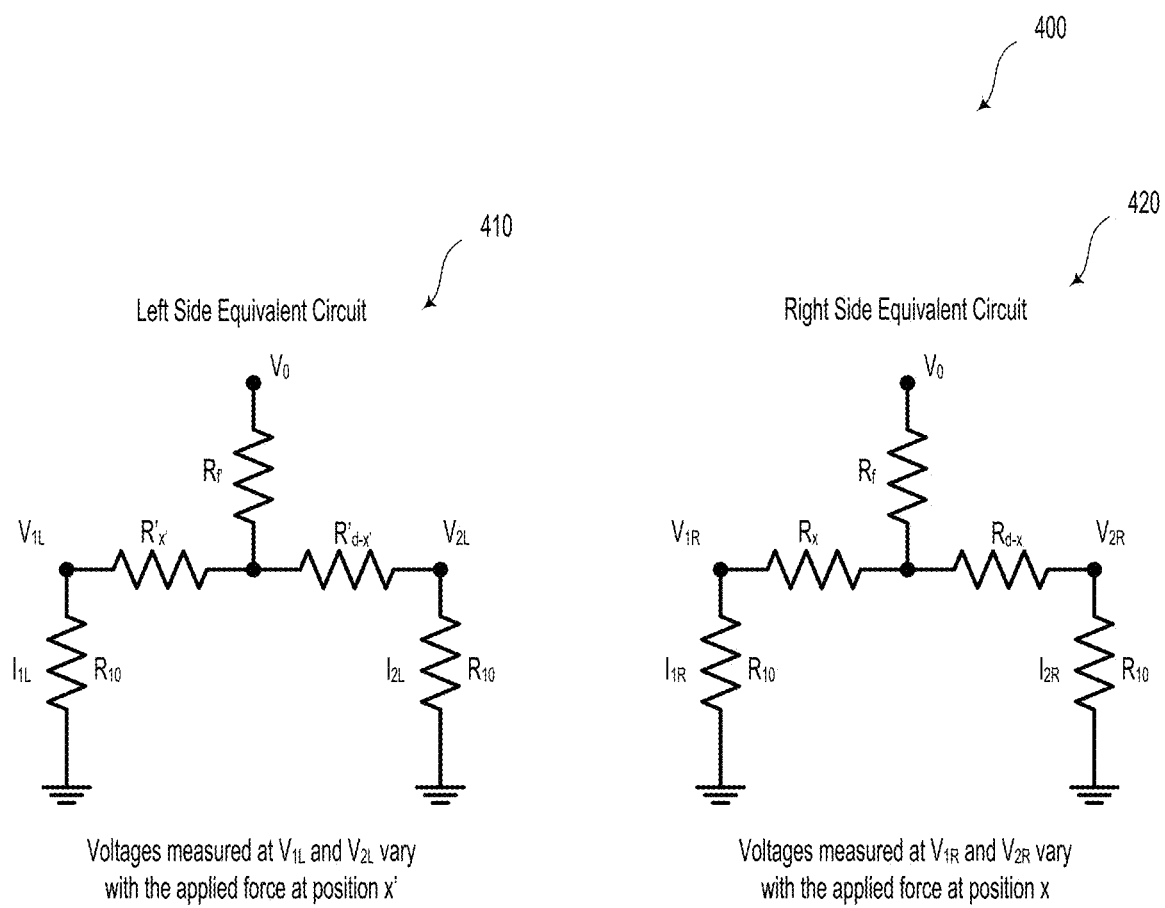
FIG. 4 illustrates equivalent circuits from the vertical force transducer system of FIG. 3, according to an example embodiment.

FIG. 4 illustrates respective equivalent circuits 400 from the vertical force transducer system 300 of FIG. 3, according to an example embodiment. The equivalent circuits 400 could represent respective sides of the vertical force transducer system 300, as illustrated and described in reference to FIG. 3. FIG. 4 illustrates a left side equivalent circuit 410 and a right side equivalent circuit 420.

Figure 5:
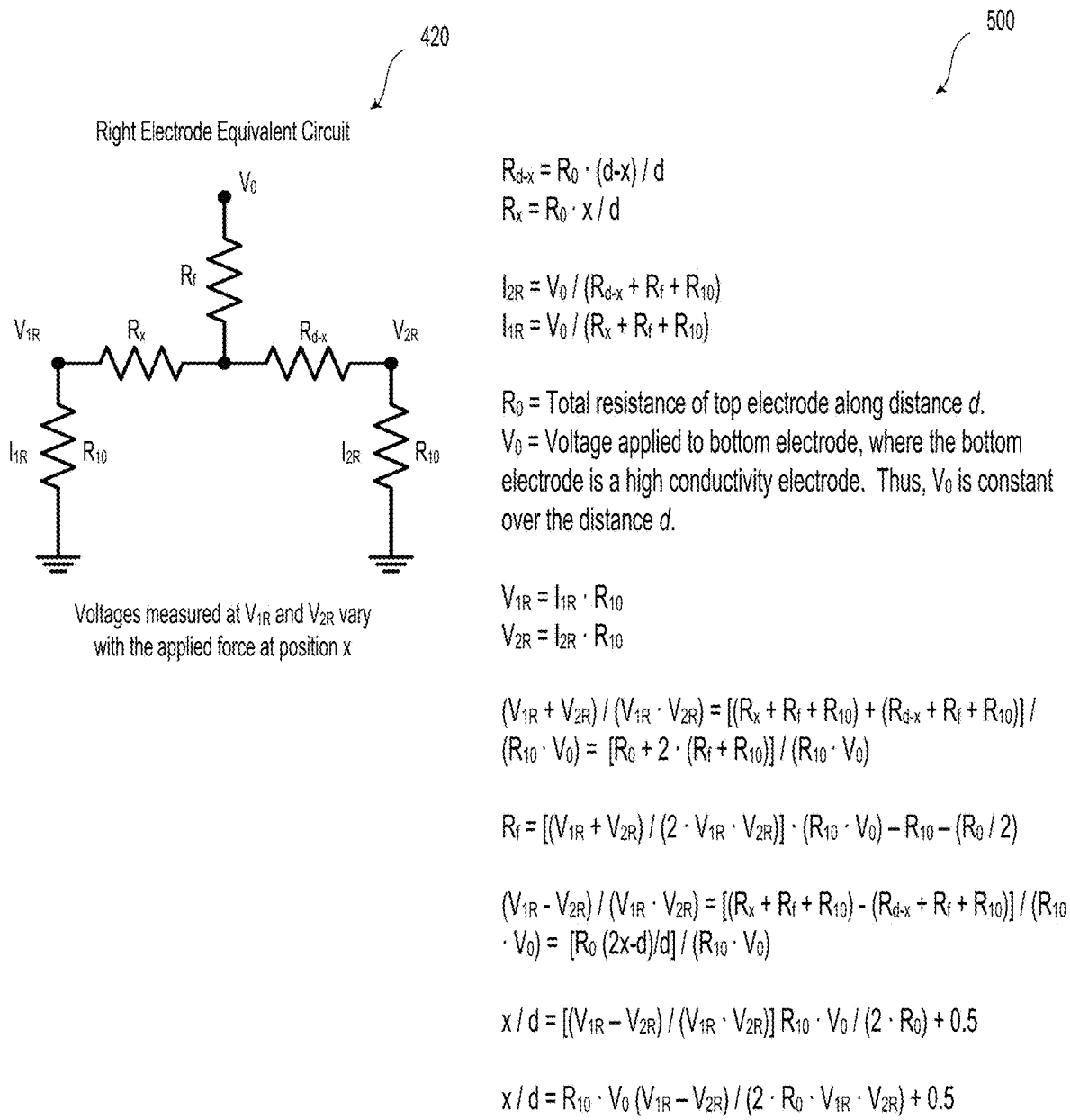
FIG. 5 illustrates mathematical expressions relating to the vertical force transducer system of FIG. 3, according to an example embodiment.

FIG. 5 illustrates mathematical expressions relating to the vertical force transducer system 300 of FIG. 3, according to an example embodiment. In some embodiments, the mathematical expressions could be utilized to calculate the location and/or the amplitude of the vertical force 10. The following expressions can be obtained by way of nodal circuit analysis:

$$R_{d-x} = R_0 \cdot (d-x)/d$$

$$R_x = R_0 \cdot x/d$$

$$I_{2R} = V_0/(R_{d-x} + R_f + R_{10})$$

$$I_{1R} = V_0/(R_x + R_f + R_{10})$$

$R_0$ is the total resistance of top electrode along distance d. $V_0$ is the voltage applied to bottom electrode, where the bottom electrode is a high conductivity electrode. Thus, $V_0$ is substantially constant over the distance d.

$$V_{1R} = I_{1R} \cdot R_{10}$$

$$V_{2R} = I_{2R} \cdot R_{10}$$

$$(V_{1R} + V_{2R})/(V_{1R} \cdot V_{2R}) = [(R_x + R_f + R_{10}) + (R_{d-x} + R_f + R_{10})]/(R_{10} \cdot V_0) = [R_0 + 2 \cdot (R_f + R_{10})]/(R_{10} \cdot V_0)$$

$$R_f = [(V_{1R} + V_{2R})/(2 \cdot V_{1R} \cdot V_{2R})] \cdot (R_{10} \cdot V_0) - R_{10} - (R_0/2)$$

$$(V_{1R} - V_{2R})/(V_{1R} \cdot V_{2R}) = [(R_x + R_f + R_{10}) - (R_{d-x} + R_f + R_{10}R)]/(R_{10} \cdot V_0) = [R_0(2x-d)/d]/(R_{10} \cdot V_0)$$

$$x/d = [(V_{1R} - V_{2R})/(V_{1R} \cdot V_{2R})]R_{10} \cdot V_0/(2 \cdot R_0) + 0.5$$

$$x/d = R_{10} \cdot V_0(V_{1R} - V_{2R})/(2 \cdot R_0 \cdot V_{1R} \cdot V_{2R}) + 0.5$$

Figure 6:
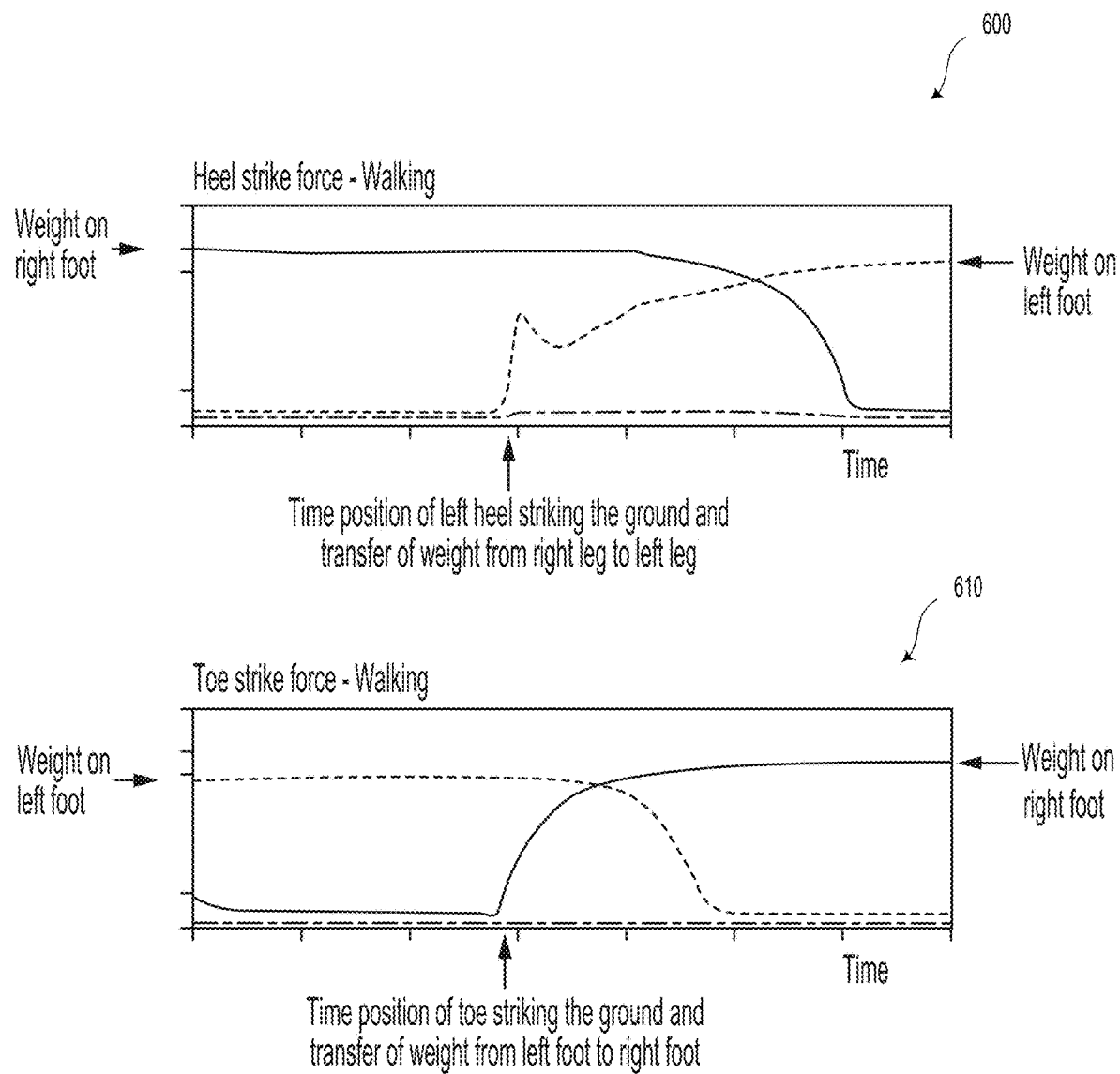
FIG. 6 illustrates force versus time measurement data, according to example embodiments.

FIG. 6 illustrates force versus time measurement data 600 and 610, according to example embodiments. The vertical force transducer systems described herein can be used to evaluate running and walking strides. FIG. 6 illustrates force data from a person walking with a standard gait where the heel hits the ground first and then the toe. The x coordinate is time in milliseconds and the y coordinate is force. Note that when the left heel hits the ground there is a sudden force impact and yet very little transfer of weight from the right foot to the left foot. Most of the force impact when walking heel-to-toe is absorbed by the body and does not effectively transfer weight from one leg to the other. In contrast, while walking so that the toe touches the ground first the body weight is smoothly transferred from one leg to the other and the force impact is greatly reduced, potentially lessening the possibility of injury or degenerative joint wear. Note also that the transfer of weight from one leg to the other happens more quickly with a toe strike. This data can be used by physical therapists to evaluate gait and to analyze recovery from joint replacement therapy.

Figure 7:
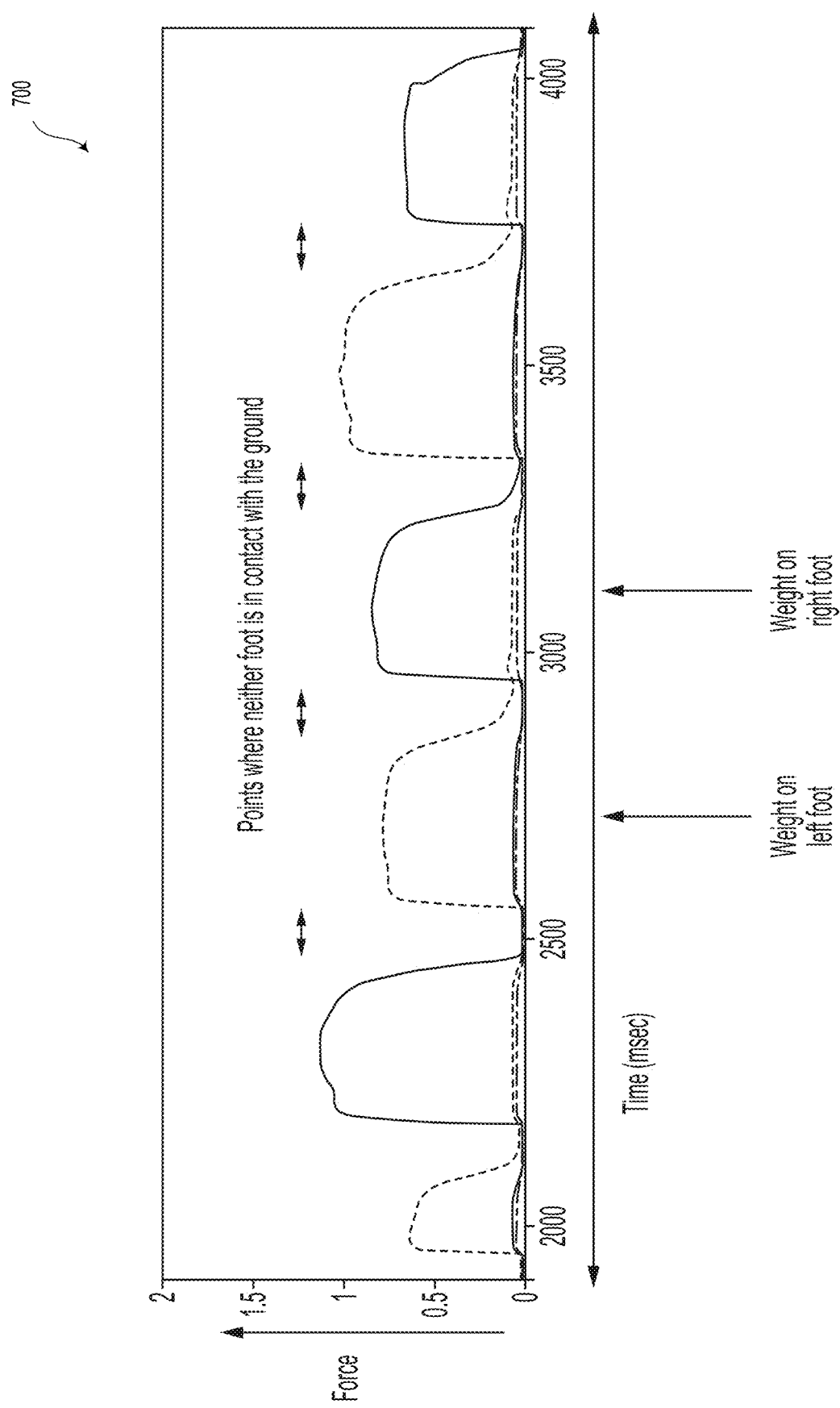
FIG. 7 illustrates force versus time measurement data, according to example embodiments.

FIG. 7 illustrates force versus time measurement data, according to example embodiments. FIG. 7 contains data of a person running on the vertical force transducer systems described herein. In this case, the runner was primarily toe striking which is evident from the absence of any heel strike impact signature. Note that in contrast to walking, there are points in time when neither foot is in contact with the ground. In certain situations, for example in professional football, this would be a time when the runner would be more vulnerable to an open field tackle. Trainers could use this data to adjust running styles and potentially to optimize athletic performance.

While example embodiments described herein relate to detecting forces based on varying voltage and/or resistance measurements, it will be understood that other ways to measure physical forces are possible and contemplated. For example, force-sensing could be performed by detecting changes in thin film capacitance, similar to applications in capacitive touch-screen technologies. In such scenarios, embodiments could include an insulator that is coated with a conductive material, which could make up the top surface 112 and/or top electrode 120. As a human body interacts with the top surface 112 and/or top electrode 120, an associated electrostatic field could be distorted or dynamically altered. In such a manner, a magnitude of physical force, which may be proportional to the distortion of the electrostatic field, could be measured and/or detected. Additionally or alternatively, piezoelectric sensing systems and methods are contemplated.

Various initialization and/or calibration methods are considered and possible within the scope of the present disclosure. For example, the force and/or position of a foot strike can be calibrated by applying a known force at regular distance intervals along the length of the vertical force transducer system 100. For example, a runner can step using just his toes (e.g., tip toe) on markers placed every 12 inches down the length of the vertical force transducer system 100. In such a scenario, the voltage differences and sums could be read out at each of these locations, and the corresponding values can then be stored in and/or compared against a look up table to determine the location and force of each foot strike for that person when they subsequently run down the length of the vertical force transducer system 100. Foot strikes that occur between the measurement locations can be determined by linear interpolation or curve fitting between adjacent locations in the lookup table.

In some embodiments, the vertical force transducer system 100 could be incorporated into a treadmill running/walking surface. For example, the vertical force transducer system 100 could be fashioned into a loop or belt that could be driven by a conventional treadmill belt drive mechanism. In such scenarios, the treadmill system could provide information about user stride length, balance, form, among other possibilities.

In yet further embodiments, the vertical force transducer system 100 could be utilized to detect and/or diagnose various physical or mental ailments. For example, individual 182 could walk along the vertical force transducer system 100 and various gait information, such as balance, step length, stride length, cadence, speed, dynamic bas, progression line, foot angle, hip angle, and/or squat performance could be provided. A medical professional or trainer could utilize such information to diagnose various conditions, including, but not limited to: cerebral palsy, Parkinson's disease, or other neuromuscular disorders. Additionally or alternatively, medical professionals may be able to ascertain recovery from medical intervention (e.g., muscle or tendon repair, knee/hip replacement, etc.) or provide improved prosthetic fitting. Other applications are possible and contemplated.

As described herein, the integrated LEDs or light strips along the length of the vertical force transducer system could illuminate at the precise locations of the user's footstrike. These locations could be stored in data files and the foot strikes can be replayed after each exercise or recalled from any past attempt. Such an LED "playback" feature could provide the ability for users to race themselves, teammates, global users, celebrity athletes, or set desired "goal" foot locations that will appear based on speed, time, and/or stride length.

In some examples, the LED lights could enable a wide variety of agility/footwork based games and drills. For example, side-to-side shuffle steps can be programmed to illuminate the light-emitter devices and turn such devices off when users place their feet within the indicated step-zones. Distinct color patterns can be used with various footwork drills due to the flexibility and programmability of the LED strips. These enhancements can improve reaction time and brain plasticity in previously unattainable ways. LED-based reaction training is not necessarily a new concept; but generally, the systems involved are not meant for actual impacts and can be damaged by being stepped on. The present system provides for users to actively use force in drills that may have previously involved only "waving" a hand or foot over an optical sensor.

In various embodiments, a coach could illuminate red, green, orange, yellow, and blue lights along the top surface at the same time and indicate that an athlete needs to turn off the orange lights and blue lights only (e.g., by stepping on or near the orange and blue LEDs). In such scenarios, integrated LED strips could allow the surface of the vertical force transducer system to provide a "smart" agility ladder. Precise footwork drills such as the "Icky Shuffle", dance moves, and other footwork exercises can be analyzed in a highly analytical manner, measuring the pace and/or counting the exact number of steps during the drill, in addition to providing detailed foot placement and balance metrics.

B. Lateral Force Transducer System

Assessing movement dynamics also requires the measurement of lateral forces. These are more difficult to measure since they cannot be measured directly by force sensors as described for the vertical forces. To measure the lateral forces requires a mobile platform with low lateral resistance to transfer the forces to sensors which measure forces stopping the lateral motion of the platform. Rigid platforms can be constructed which rest upon bearing surfaces which allow frictionless motion of the platform. When a person walks or runs on this platform the platform will slide in a direction opposite to the person motion. If the platform is held in place by a restraining bracket then the lateral force will be transferred to this bracket. A force transducer placed between the platform and the bracket will then measure the lateral force due to the walking or running motion of the platform. Forces in any direction can be measured by mounting the platform on bearing surface and constraining the motion in all four horizontal directions.

Figure 8:
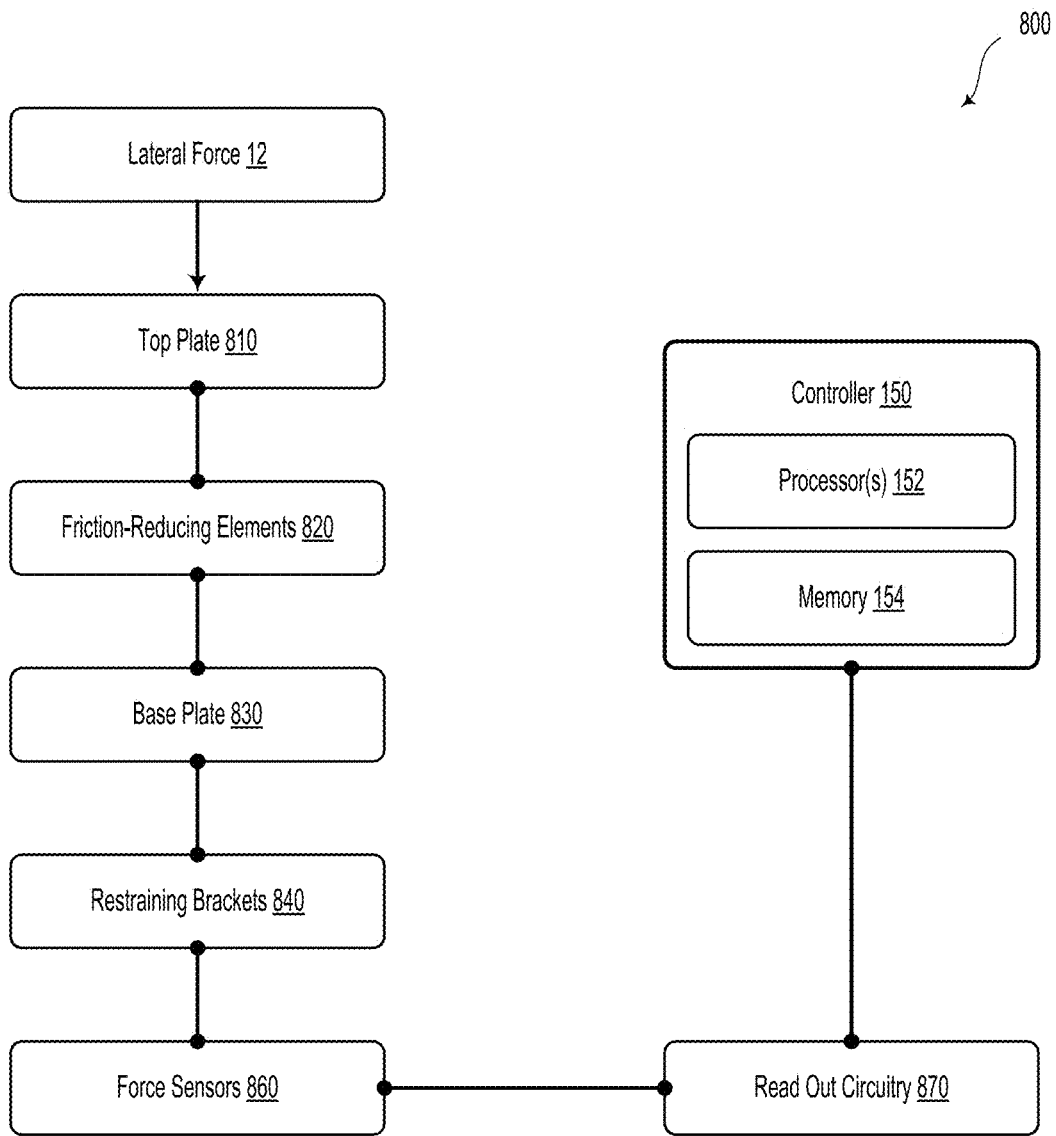
FIG. 8 illustrates a lateral force transducer system, according to an example embodiment.

FIG. 8 illustrates a lateral force transducer system 800, according to an example embodiment. The lateral force transducer system 800 includes a base plate 830 and a top plate 810 slidably coupled to the base plate 830.

In some embodiments, the lateral force transducer system 800 may also include a plurality of friction-reducing elements 820 disposed between the base plate 830 and the top plate 810. In various embodiments, the friction-reducing elements 820 could include at least one of: a ball bearing, a roller bearing, a fluid bearing, or skate wheels. In such scenarios, at least 64 friction-reducing elements 820 could be disposed in a planar array between the base plate 830 and the top plate 810. It will be understood that other devices and/or mechanisms to provide a surface that moves laterally without friction are possible and contemplated.

The lateral force transducer system 800 also includes at least two restraining brackets 840 disposed proximate to opposite sides of the base plate 830. In such scenarios, the restraining brackets 840 are configured to restrict lateral movement of the top plate 810 with respect to the base plate 830.

The lateral force transducer system 800 additionally includes a force sensor 860 coupled to each restraining bracket 840. Each force sensor 860 is configured to measure a lateral force 12 applied to the top plate 810 and transferred to a given restraining bracket 840.

The lateral force transducer system 800 also includes read out circuitry 870 configured to provide information indicative of the amplitude of the lateral force 12 and a direction of the lateral force 12.

In some embodiments, the lateral force transducer system 800 may additionally include a controller (e.g., controller 150) having at least one processor (e.g., processor 152) and a memory (e.g., memory 154). In some embodiments, the processor can execute program instructions stored in the memory so as to carry out operations.

The operations include receiving, from the read out circuitry 870, information indicative of the lateral force 12 applied to the top plate 810.

The operations may additionally include determining, based on the received information, an amplitude of the lateral force 12.

The operations may additionally include determining, based on the received information, a direction of the lateral force 12.

In some embodiments, the lateral force transducer system 800 may include a base plate 830 with four sides. In such scenarios, the at least two restraining brackets 840 could include four total restraining brackets. In those cases, the restraining brackets 840 could be disposed proximate to each side of the base plate 830 (e.g., along the North, South, East, West sides of the base plate 830).

In some embodiments, the direction of the lateral force 12 could include a force vector parallel to the base plate 830.

In some embodiments, the top plate 810 could include a plurality of bearing tracks configured to slidably interact with the friction-reducing elements 820.

Figure 9:
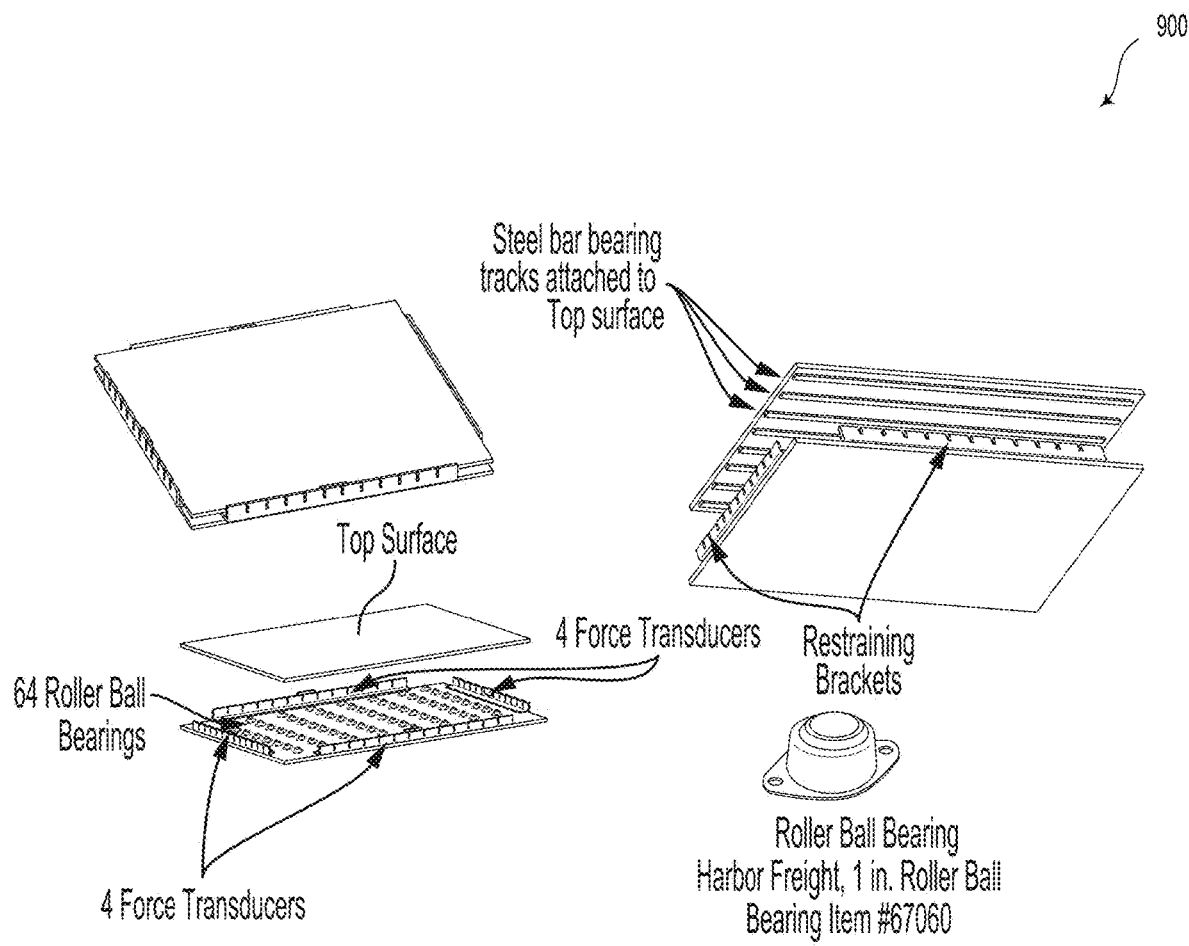
FIG. 9 illustrates a two-dimensional lateral force transducer system, according to an example embodiment.

FIG. 9 illustrates a two-dimensional lateral force transducer system 900, according to an example embodiment. The two-dimensional lateral force transducer system 900 is a size-scalable force sensing platform designed to measure horizontal forces during kinesthetic movement. The two-dimensional lateral force transducer system 900 could be formed by two 4'×4'¾" plywood boards, sixty four 1" ball-bearing rollers, eight 46"×1"×0.0.125" steel bars, four 3' aluminum L brackets, and four force sensors attached to circuit boards. The 64 roller ball bearing assemblies (e.g., Harbor Freight, 1 in. Roller Ball Bearing) are screwed down in an equidistant 8×8 grid across the bottom plywood board. The eight steel bars are screwed into the underside of the top plywood board, in parallel, aligned directly on top of the same 8×8 grid as the ball bearing rollers. The top plywood board lays directly on top of the bottom plywood board with the steel tracks on the underside of the top board providing a frictionless surface for the ball bearings to move and prevents potential indentations in the plywood. All four aluminum L brackets are also screwed down to the bottom plywood boards along the four edges and extended very slightly off the platform. Force sensors are attached to the center of the aluminum L brackets along all four sides of the bottom board.

Alternatives to using ball-bearing rollers or other bearing assemblies to provide a low friction interface between the top and bottom boards are: (1) A polymer gel with low lateral or shear force viscosity such as SHOCKtec® Gel, from Shocktec, Inc.; (2) an air bearing surface; (3) a captured liquid interface (e.g., similar to a waterbed) placed between the top and bottom surface. All these alternatives have low lateral resistance to small displacements of the top surface platform and allow the lateral force to be applied directly to the force sensor, similar to the bearing assembly design mentioned above.

As a user moves while on the platform, the extra space provided by the L brackets allows very slight movements of the top board which pushes the board into the force sensor pressure plates in the corresponding direction of the forces applied. The roller ball assemblies allow movement—and detection of forces—in all 4 directions simultaneously. The amount of movement is virtually undetectable by the user to prevent compensatory movements to stabilize the board and can provide an experience as similar as possible to kinesthetic movement across flat ground. These forces are recorded as "North, South, East, or West" horizontal forces and the total horizontal force can be calculated by combining the force vectors recorded by each direction during the contact with the board.

Figure 10:
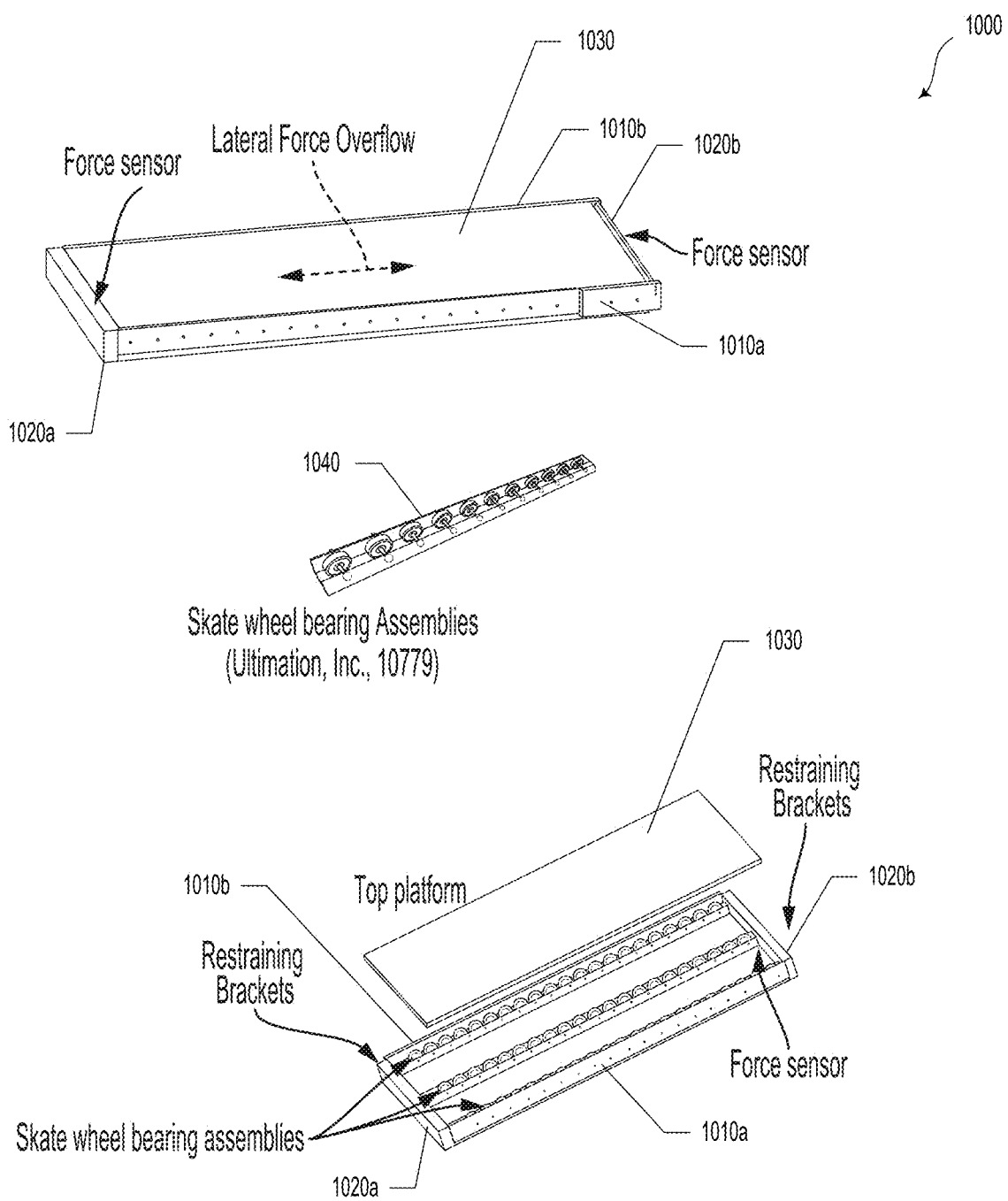
FIG. 10 illustrates a one-dimensional lateral force transducer system, according to an example embodiment.

FIG. 10 illustrates a one-dimensional lateral force transducer system 1000, according to an example embodiment. Lateral force platforms can be constructed using or cylindrical bearing assemblies (Skate Wheel, Ultimation, 5 foot, conveyor rails, 10779). Skate wheel assemblies 1040 allow force measurements both along the direction of motion and in the opposite direction. They also provide a greater contact area between the bearing surface and the top platform 1030 reducing the possibility of wear. By taking readings from multiple sensors, force vectors in any direction can be measured.

In some embodiments, the side restraining brackets 1010a and 1010b parallel to the lateral force flow in FIG. 10 could include a low friction covering or coating, such as polytetrafluoroethylene (PTFE), to reduce frictional forces that might impede the lateral motion of the top platform 1030. Additionally or alternatively, the side restraining brackets 1010a and 1010b could incorporate wheel bearing assemblies 1040 to constrain the side-to-side motion of the top platform 1030 but still allow low friction movement in the lateral direction.

In some embodiments, the force sensor restraining brackets 1020a and 1020b illustrated in FIG. 10 could incorporate a compressible elastomer sheet or mechanical spring assemblies. The clamping force applied to the restraining brackets 1020a and 1020b during assembly of the lateral force platform can provide an adjustable preloading of the force sensors; that is, they will register a force with no additional lateral force applied to the top platform. This embodiment of the lateral force platform will allow each force sensor to measure additional forces applied to the top platform in either the forward or reverse directions.

C. Vertical and Lateral Force Transducer System

Systems that can measure both lateral and vertical forces are now described.

Figure 11:
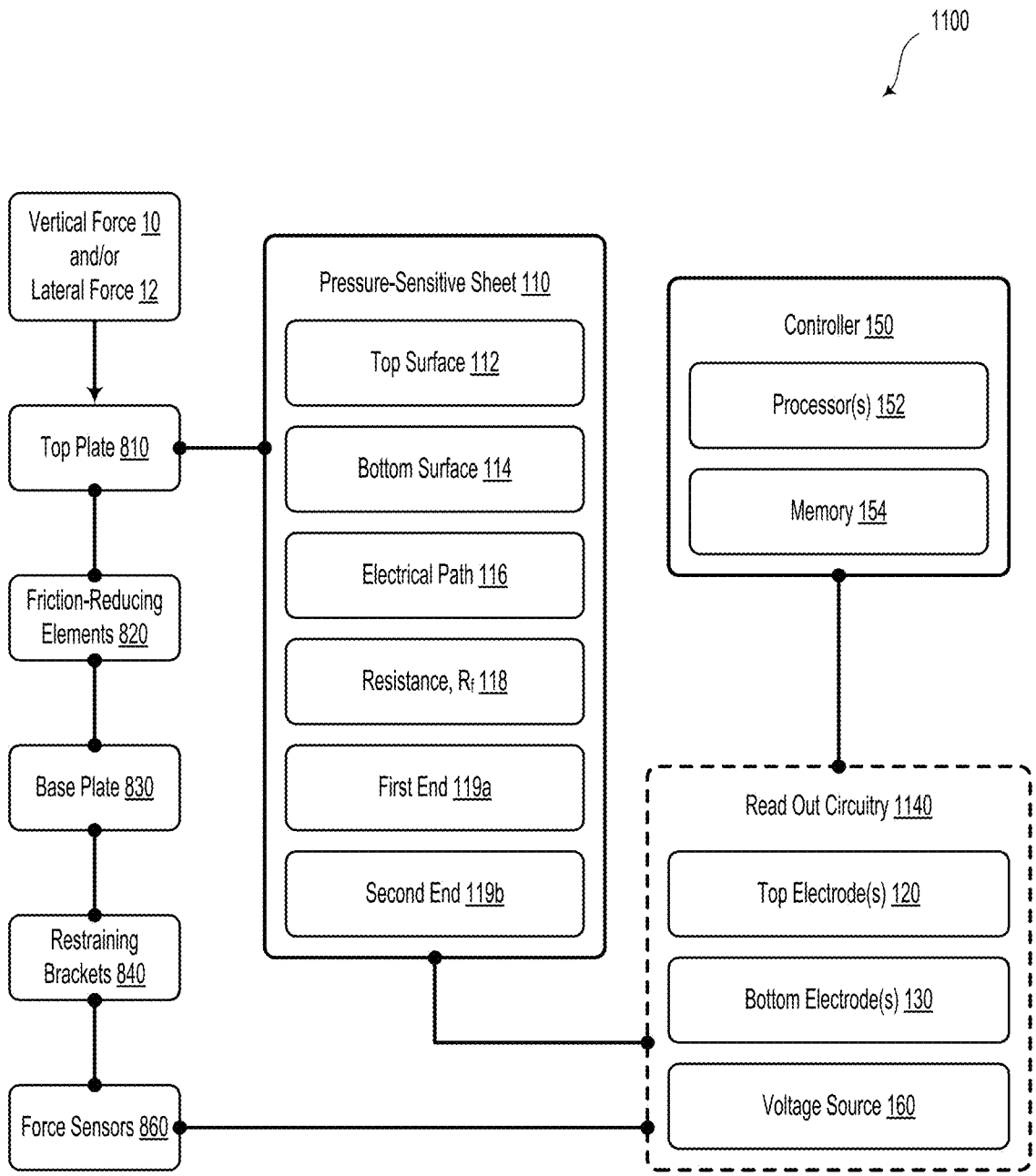
FIG. 11 illustrates a vertical and lateral force transducer system, according to an example embodiment.

FIG. 11 illustrates a vertical and lateral force transducer system 1100, according to an example embodiment. The vertical and lateral force transducer system 1100 could include elements of the vertical force transducer system 100, 200, 220, or 300 as illustrated and described in reference to FIGS. 1A, 1B, 2A, 2B, and 3. Additionally, the vertical and lateral force transducer system 1100 could include elements of the lateral force transducer system 800, 900, and/or 1000, as illustrated and described in FIGS. 8, 9, and 10.

The vertical and lateral force transducer system 1100 includes a base plate (e.g., base plate 830) and a top plate (e.g., top plate 810) slidably coupled to the base plate. The top plate includes a pressure-sensitive sheet (e.g., pressure-sensitive sheet 110) that extends along a first axis. The pressure-sensitive sheet includes a top surface and a bottom surface. In such scenarios, a vertical force (e.g., vertical force 10) applied at a location along at least one of the top surface (e.g., top surface 112) or the bottom surface (e.g., bottom surface 114) forms an electrical path between the top surface and the bottom surface having a resistance, $r_f$, that is inversely proportional to an amplitude of the vertical force 10.

The vertical and lateral force transducer system 1100 may additionally include a plurality of friction-reducing devices (e.g., friction-reducing elements 820) disposed between the base plate and the top plate.

The vertical and lateral force transducer system 1100 may further include at least two restraining brackets (e.g., restraining brackets 840) disposed proximate to opposite sides of the base plate. In such a scenario, the restraining brackets are configured to restrict lateral movement of the top plate with respect to the base plate.

The vertical and lateral force transducer system 1100 further includes a force sensor (e.g., force sensor 860) coupled to each restraining bracket. Each force sensor is configured to measure a lateral force (e.g., lateral force 12) applied to a given restraining bracket.

The vertical and lateral force transducer system 1100 also include read out circuitry (e.g., read out circuitry 1140). The read out circuitry could include a top electrode (e.g., top electrode 120 extending along the top surface of the pressure-sensitive sheet.

The vertical and lateral force transducer system 1100 further includes a bottom electrode (e.g., bottom electrode 130) extending along the bottom surface of the pressure-sensitive sheet.

In some embodiments, the vertical and lateral force transducer system 1100 could include a voltage source (e.g., voltage source 160) configured to provide a reference voltage, $V_0$, between the top electrode and the bottom electrode. wherein the read out circuitry is configured to provide information indicative of: the amplitude of the vertical force, the location of the vertical force, the amplitude of the lateral force, and a direction of the lateral force.

The vertical and lateral force transducer system 1100 may include a controller having at least one processor and a memory.

The processor executes program instructions stored in the memory so as to carry out operations. The operations include receiving, from the read out circuitry, information indicative of the vertical and lateral forces applied to the top plate. The operations also include determining, based on the received information, an amplitude of the vertical force.

In some embodiments, the operations could include determining, based on the received information, a location of the vertical force along the first axis of the pressure-sensitive sheet.

The operations may additionally include determining, based on the received information, an amplitude of the lateral force.

The operations may further include determining, based on the received information, a direction of the lateral force.

In some embodiments, the base plate includes four sides. In such scenarios, at least two restraining brackets may actually describe four restraining brackets (one for each side the base plate. In such scenarios, the restraining brackets could be disposed proximate to each side of the base plate.

In various embodiments, the direction of the lateral force 12 could include a force vector parallel to the base plate.

In some examples, the friction-reducing elements could include at least one of: a ball bearing, a roller bearing, a fluid bearing, or skate wheels. As just one example, at least 64 friction-reducing elements could be disposed in a planar array between the base plate and the top plate.

In some embodiments, the top plate includes a plurality of bearing tracks configured to slidably interact with the friction-reducing elements.

In some embodiments, the vertical force transducer system and the lateral force transducer could be configured to measure both horizontal and vertical forces, creating a complete force profile of an individual foot strike and other athletic movements including change of direction(cuts), jumps, and sudden deaccelerations.

D. Applications of the Vertical and Lateral Force Measurements

Systems described herein represent new and better ways to analyze movement fundamentals and assess the forces generated by all levels of human movement, from elderly patients undergoing physical therapy to athletes seeking the apexes of human ability. Force profiles can help physical therapists by taking baseline measurements pre/post surgery, or as part of their initial body assessment. These baselines can dictate both the amount of rehabilitation needed to reach pre-injury performance as well as set realistic expectations based on the force readings of others in their demographic.

Systems described herein may beneficially provide athletes and their training staff the opportunity to use previously recorded metrics from current and previous performance in movement tests to optimize their training and scores in competition. Data on force generated through movement may give training staff early warning signs regarding injury, fatigue, or suggest specific exercises that an athlete should focus on to improve their performance.

A common metric to measure speed and acceleration for all positions in American Football is the 40 yard dash. For aspiring professional football players, fractions of a second in a 40 yard dash time can be a factor in draft position and may represent a difference of millions of dollars in professional contracts. Traditionally, the 40 yard dash has been measured by stopwatches and laser activated timing gates. With systems described herein, complex metrics of each individual foot strike can be analyzed by coaches and trainers. Different lengths of a vertical force transducer system (e.g., system 100), a lateral force transducer system (e.g., system 800), and/or a vertical and lateral force transducer system (e.g., system 1100) can be used depending on the resources and training space available to the user. As an example, the path length could range from a 5'-long starting block segment that measures the acceleration and foot-falls of the first few footstrikes plus the horizontal forces of their take off, to a complete 40 yard-length segment that tracks data on every footfall of the entire exercise.

In professional athletics, there is a great need for both the rehabilitation of lower-body injuries as well as proper training to reach peak performance. The rigors of high-level athletic competition propel the human body to the limits of our physical capabilities while also resulting in higher rates of devastating injury. As football players have gotten stronger, faster, and more explosive, the risk of career-altering injuries such as ACL tears has also increased. One such injury to a star athlete can dramatically change the outcome of their career, as well as possibly affect the success of the injured athlete's team.

Anterior cruciate ligament (ACL) tears are one of the most common catastrophic injuries suffered by athletes of all ages. These injuries are most likely to occur during sports involving sudden changes of direction, such as basketball, football, and soccer. Recovery time for an ACL reconstruction typically takes no less than 9 months and some research indicates a more realistic timeline may be more than two years. In some cases, the athlete never returns to pre-injury levels of activity or function. Due to the severity of this injury and the lengthy and laborious rehabilitation process, there has been recent emphasis in developing realistic and evidence-based "Return to Sport" guidelines for athletes trying to return to athletic competition.

Return to Sport guidelines involve helping athletes reach pre-injury baseline levels of function, primarily post reconstructive ACL surgery, before returning to intensive activity. One of the most common Return To Sport tests is the "single leg hop test". In this test, the athlete jumps forward with one leg as far as possible and lands with the same leg. The distance is recorded for each jump and the process is repeated twice, with both the injured and noninjured leg. Despite this being an industry standard test, there is some conflicting research on the efficacy of the "single leg hop test" for ACL reconstruction recovery. Research has shown that the degradation of function in the non-injured leg during the 6-12+ month rehabilitation process may impact the efficacy of this test as a Return To Sport standard.

Embodiments described herein can help inform new Return To Sport guidelines by giving athletic teams, athletic trainers, physical therapists, and other fitness professionals access to data that compiles the complete force profile (e.g., combination of both vertical and lateral force) of a given athlete. Coaches and Physical Therapists will gain access to previously unattainable data from these platforms and develop complete force profiles of virtually any form of body movement exercise. The complete force profiles measured by these systems will be a novel resource to validate and enhance current testing criteria and potentially influence new Return To Sport guidelines across the entire sports world.

III. Example Methods

Figure 12:
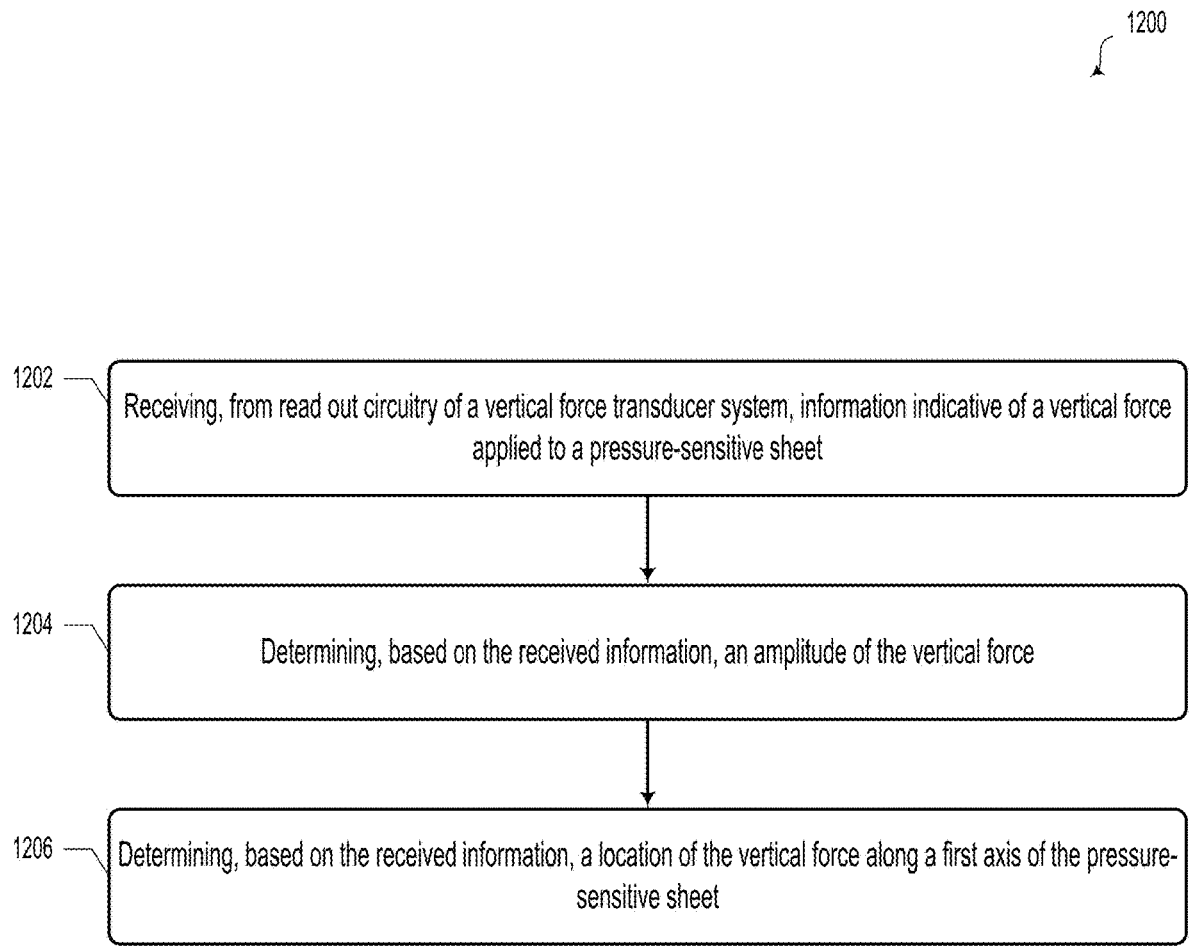
FIG. 12 illustrates a method, according to an example embodiment.

FIG. 12 illustrates a method 1200, according to an example embodiment. It will be understood that the method 1200 may include fewer or more steps or blocks than those expressly illustrated or otherwise disclosed herein. Furthermore, respective steps or blocks of method 1200 may be performed in any order and each step or block may be performed one or more times. In some embodiments, some or all of the blocks or steps of method 1200 may be carried out by a vertical force transducer system (e.g., vertical force transducer system 100). It will be understood that other scenarios are possible and contemplated within the context of the present disclosure.

Block 1202 includes receiving, from read out circuitry of a vertical force transducer system, information indicative of a vertical force applied to a pressure-sensitive sheet.

Block 1204 includes determining, based on the received information, an amplitude of the vertical force.

Block 1206 includes determining, based on the received information, a location of the vertical force along a first axis of the pressure-sensitive sheet.

Figure 13:
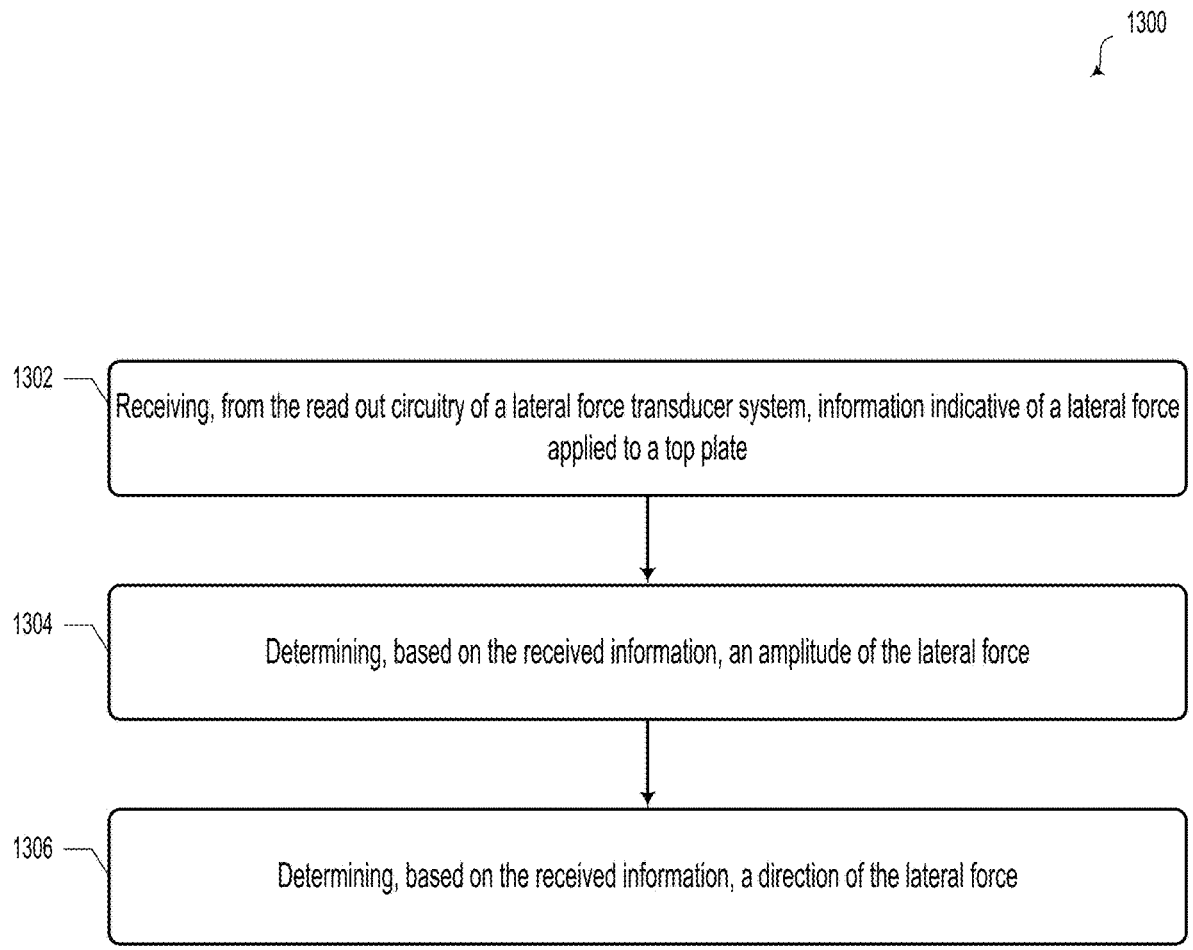
FIG. 13 illustrates a method, according to an example embodiment.

FIG. 13 illustrates a method 1300, according to an example embodiment. It will be understood that the method 1300 may include fewer or more steps or blocks than those expressly illustrated or otherwise disclosed herein. Furthermore, respective steps or blocks of method 1300 may be performed in any order and each step or block may be performed one or more times. In some embodiments, some or all of the blocks or steps of method 1300 may be carried out by a lateral force transducer system (e.g., lateral force transducer system 800). It will be understood that other scenarios are possible and contemplated within the context of the present disclosure.

Block 1302 includes receiving, from the read out circuitry of a lateral force transducer system, information indicative of a lateral force applied to a top plate.

Block 1304 includes determining, based on the received information, an amplitude of the lateral force.

Block 1306 includes determining, based on the received information, a direction of the lateral force.

Figure 14:
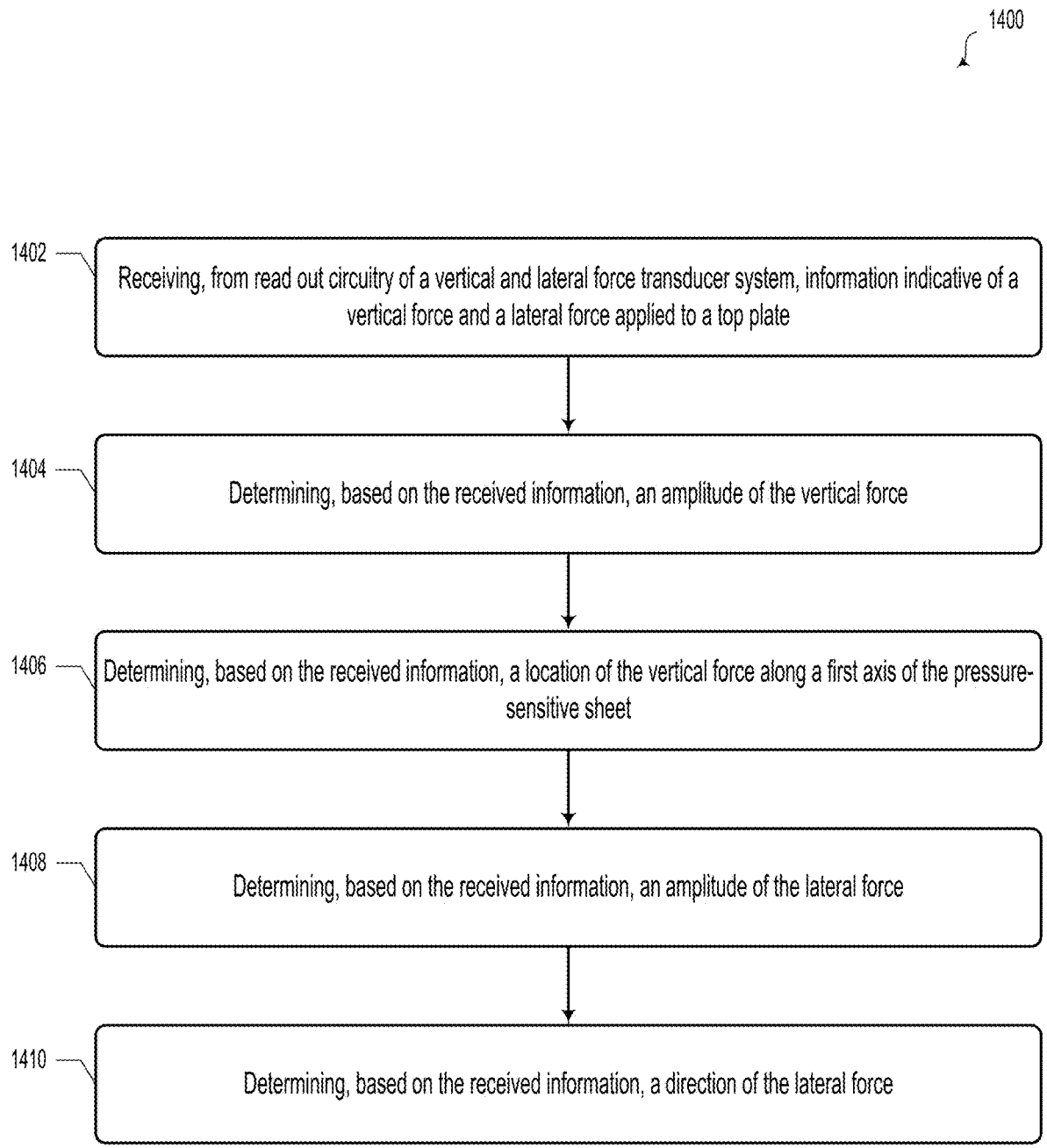
FIG. 14 illustrates a method, according to an example embodiment.

FIG. 14 illustrates a method 1400, according to an example embodiment. It will be understood that the method 1400 may include fewer or more steps or blocks than those expressly illustrated or otherwise disclosed herein. Furthermore, respective steps or blocks of method 1400 may be performed in any order and each step or block may be performed one or more times. In some embodiments, some or all of the blocks or steps of method 1400 may be carried out by a vertical and lateral force transducer system (e.g., vertical and lateral force transducer system 1100). It will be understood that other scenarios are possible and contemplated within the context of the present disclosure.

Block 1402 includes receiving, from read out circuitry of a vertical and lateral force transducer system, information indicative of a vertical force and a lateral force applied to a top plate;

Block 1404 includes determining, based on the received information, an amplitude of the vertical force.

Block 1406 includes determining, based on the received information, a location of the vertical force along a first axis of the pressure-sensitive sheet.

Block 1408 includes determining, based on the received information, an amplitude of the lateral force.

Block 1410 includes determining, based on the received information, a direction of the lateral force.

IV. Additional Example Embodiments

When measuring forces generated from running movements, vertical and lateral forces generated by a runner's left and right feet typically occur at different times (e.g., in an alternating right-left-right-left manner). For example, after an initial starting phase (e.g., initial take-off), the runner's feet alternate contact with the ground and typically do not land on or push off the ground at the same time.

However, in some scenarios, lateral forces may be produced by both feet simultaneously during the initial starting phase. For example, during various track and field events, starting blocks may be utilized to provide that all participants start from equal starting positions and also to prevent the athletes' feet from slipping upon take-off. In such scenarios, both feet may be placed on independent starting blocks that can be anchored to the running surface. As such, the starting blocks can allow simultaneous lateral force impulses from both legs. The starting blocks can be adjusted to different angles and foot-spacing based on the physical characteristics and preferences of the athlete.

Within the context of the present disclosure, valuable data can be collected by attaching the starting blocks to lateral force transducer platforms. Such lateral force transducer platforms may be configured to simultaneously and independently measure the lateral forces of both feet generated during an athlete's take-off from the starting blocks. In an example embodiment, each starting block may be coupled to a separate lateral force platform. In such scenarios, the timing and force transients of the left and right foot may be measured independently. Additionally or alternatively, the vertical and/or lateral force transducers described herein may be coupled or affixed directly into or onto the starting blocks themselves.

Track and field events are routinely decided by hundredths of seconds, making precise data on power, speed, and reaction time extremely valuable to coaches and athletes of all levels. Accordingly, quantitative data from lateral force transducers mounted on starting blocks could give athletes, trainers, and coaches previously unavailable metrics on an athlete's explosive power and reaction time relative to the starting gun. Additionally or alternatively, such embodiments may inform important adjustments to the starting block angle, length between blocks, and transference of lateral force impulse from left to right foot, to ensure an athlete is producing their optimal force upon takeoff.

Figure 15:
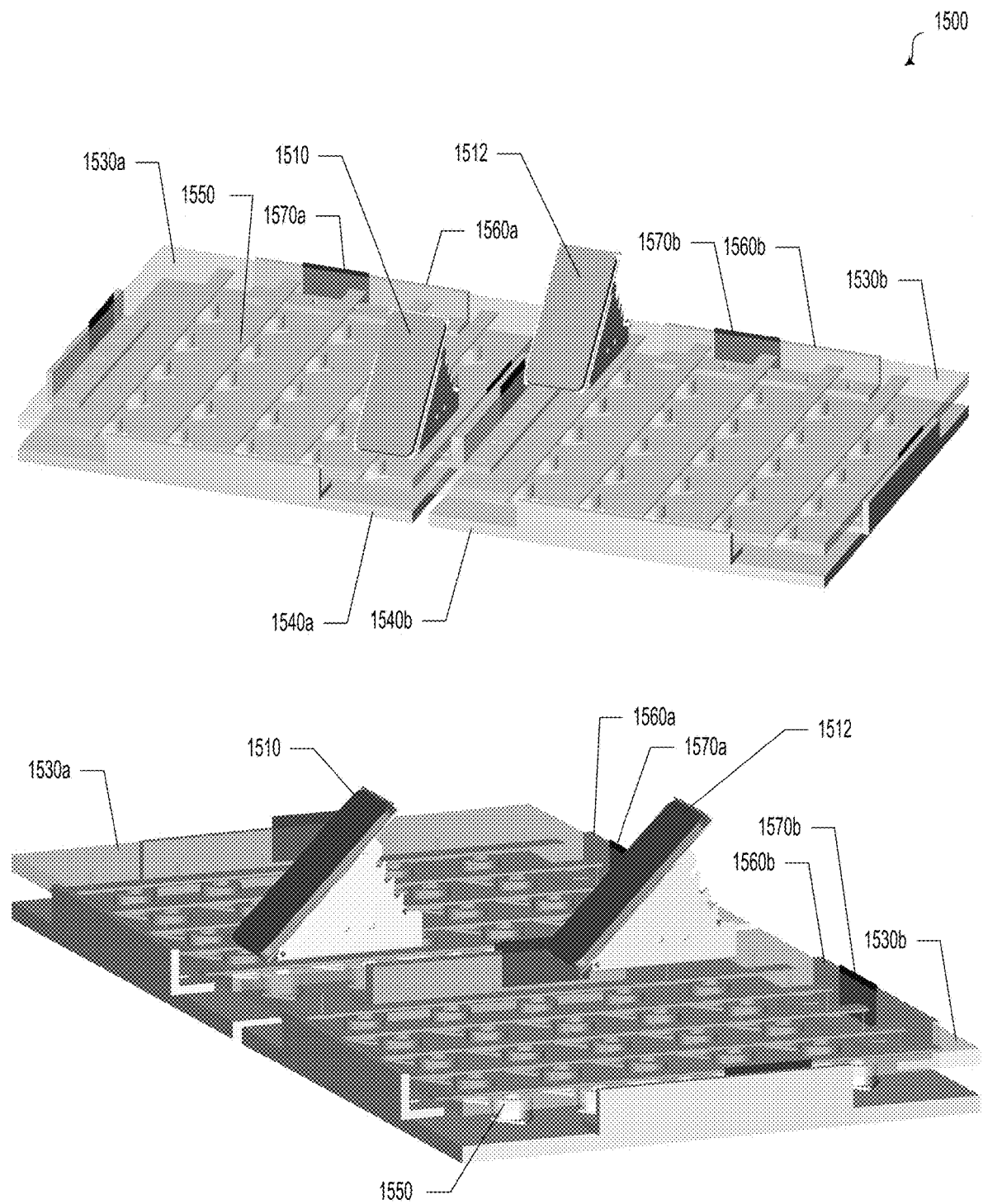
FIG. 15 illustrates a lateral force transducer system, according to an example embodiment.

FIG. 15 illustrates a lateral force transducer system 1500, according to an example embodiment. Lateral force transducer system 1500 could include elements that may be similar or identical to lateral force transducer system 800, two-dimensional lateral force transducer system 900, and/or one-dimensional lateral force transducer system 1000, as illustrated and described in relation to FIGS. 8, 9, and 10, respectively.

According to an example embodiment, the lateral force transducer system 1500 includes a base plate (e.g., base plate 1540a and 1540b). It will be recognized that while FIG. 15 illustrates two base plates, a single base plate (e.g., common base plate) could be utilized in some embodiments. The base plate could be configured to be removably attached to a running surface (e.g., track surface). In some embodiments, the base plate could be embedded in or recessed into the running surface so as to provide a flat walking/running surface.

In such scenarios, the lateral force transducer system 1500 includes a first top plate 1530a, which may be slidably coupled to the base plate 1540a. Additionally, the lateral force transducer system 1500 includes a second top plate 1530b that is slidably coupled to the base plate 1540b.

The lateral force transducer system 1500 also includes a first starting block 1510 and a second starting block 1512. The first starting block 1510 could be affixed or otherwise coupled to the first top plate 1530a. The second starting block 1512 could be affixed or otherwise coupled to the second top plate 1530b.

In some embodiments, lateral force transducer system 1500 could include a plurality of friction-reducing elements 1550 disposed between the first base plate 1540a and the first top plate 1530a and between the second base plate 1540b and the second top plate 1530a.

The lateral force transducer system 1500 also includes a first restraining bracket 1560a configured to restrict lateral movement of the first top plate 1530a with respect to the base plate 1540a. Furthermore, the lateral force transducer system 1500 includes a second restraining bracket 1560b configured to restrict lateral movement of the second top plate 1530b with respect to the base plate 1540b.

Additionally, the lateral force transducer system 1500 includes a force sensor 1570 coupled to each restraining bracket 1560. For example, a first force sensor 1570a could be coupled to the first restraining bracket 1560a and a second force sensor 1570b could be coupled to the second restraining bracket 1560b. Each force sensor 1570a and 1570b is configured to measure a lateral force applied to the respective top plate 1530a and 1530b and transferred to a given restraining bracket 1560a and 1560b.

Yet further, the lateral force transducer system 1500 includes read out circuitry configured to provide information indicative of an amplitude of the lateral force and a direction of the lateral force. For example, the read out circuitry could include an ADC (e.g., ADC 156) and/or a controller (e.g., controller 150). Additionally or alternatively, the lateral force transducer system 1500 could be configured to be operably coupled and/or communicatively coupled to another computing device.

The particular arrangements shown in the Figures should not be viewed as limiting. It should be understood that other embodiments may include more or less of each element shown in a given Figure. Further, some of the illustrated elements may be combined or omitted. Yet further, an illustrative embodiment may include elements that are not illustrated in the Figures.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

While various examples and embodiments have been disclosed, other examples and embodiments will be apparent to those skilled in the art. The various disclosed examples and embodiments are for purposes of illustration and are not intended to be limiting, with the true scope being indicated by the following claims.

What is claimed is:

1. A lateral force transducer system, comprising:
    a base plate;
    a top plate slidably coupled to the base plate;
    a plurality of friction-reducing elements disposed between the base plate and the top plate;
    a plurality of restraining brackets coupled to the base plate, wherein the restraining brackets are preloaded by a compressible elastomer sheet or a mechanical spring assembly to restrict lateral movement of the top plate with respect to the base plate;
    a force sensor coupled to each restraining bracket, wherein each force sensor is configured to measure a lateral force applied to the top plate and transferred to a given restraining bracket; and
    read out circuitry configured to provide information indicative of an amplitude of the lateral force and a direction of the lateral force.

2. The lateral force transducer system of claim 1, further comprising a controller having at least one processor and a memory, wherein the processor executes program instructions stored in the memory so as to carry out operations, the operations comprising:
    receiving, from the read out circuitry, information indicative of the lateral force applied to the top plate;
    determining, based on the received information, an amplitude of the lateral force; and
    determining, based on the received information, a direction of the lateral force.

3. The lateral force transducer system of claim 1, wherein the base plate comprises four sides, wherein the plurality of restraining brackets comprises four restraining brackets, and wherein the restraining brackets are disposed proximate to each side of the base plate.

4. The lateral force transducer system of claim 3, wherein the direction of the lateral force comprises a force vector parallel to the base plate.

5. The lateral force transducer system of claim 1, wherein the friction-reducing elements comprise at least one of: a ball bearing, a roller bearing, a fluid bearing, or skate wheels.

6. The lateral force transducer system of claim 5, wherein a plurality of friction-reducing elements are disposed in a planar array between the base plate and the top plate.

7. The lateral force transducer system of claim 1, wherein the top plate comprises a plurality of bearing tracks configured to slidably interact with the friction-reducing elements.

8. A vertical and lateral force transducer system, comprising:
    a base plate;
    a top plate slidably coupled to the base plate, wherein the top plate comprises:
        a pressure-sensitive sheet that extends along a first axis, wherein the pressure-sensitive sheet comprises a top surface and a bottom surface, wherein a vertical force applied at a location along at least one of the top surface or the bottom surface forms an electrical path between the top surface and the bottom surface having a resistance, $r_f$, that is inversely proportional to an amplitude of the vertical force;
    a plurality of friction-reducing elements disposed between the base plate and the top plate;

a plurality of restraining brackets coupled to the base plate, wherein the restraining brackets are preloaded by a compressible elastomer sheet or a mechanical spring assembly to restrict lateral movement of the top plate with respect to the base plate;

a force sensor coupled to the at least one restraining bracket, wherein each force sensor is configured to measure a lateral force applied to a given restraining bracket; and read out circuitry comprising:
- a top electrode extending along the top surface of the pressure-sensitive sheet;
- a bottom electrode extending along the bottom surface of the pressure-sensitive sheet; and
- a voltage source configured to provide a reference voltage, $V_0$, between one of: the top electrode or the bottom electrode and a ground reference, wherein the read out circuitry is configured to provide information indicative of: the amplitude of the vertical force, the location of the vertical force, the amplitude of the lateral force, and a direction of the lateral force.

9. The vertical and lateral force transducer system of claim 8, further comprising a controller having at least one processor and a memory, wherein the processor executes program instructions stored in the memory so as to carry out operations, the operations comprising:

receiving, from the read out circuitry, information indicative of the vertical and lateral forces applied to the top plate;

determining, based on the received information, an amplitude of the vertical force;

determining, based on the received information, a location of the vertical force along the first axis of the pressure-sensitive sheet determining, based on the received information, an amplitude of the lateral force; and determining, based on the received information, a direction of the lateral force.

10. The vertical and lateral force transducer system of claim 8, wherein the base plate comprises four sides, wherein the at least one restraining bracket comprises four restraining brackets, and wherein the restraining brackets are disposed proximate to each side of the base plate.

11. The vertical and lateral force transducer system of claim 10, wherein the direction of the lateral force comprises a force vector parallel to the base plate.

12. The vertical and lateral force transducer system of claim 8, wherein the friction-reducing elements comprise at least one of: a ball bearing, a roller bearing, a fluid bearing, or skate wheels.

13. The vertical and lateral force transducer system of claim 12, wherein a plurality of friction-reducing elements are disposed in a planar array between the base plate and the top plate.

14. The vertical and lateral force transducer system of claim 8, wherein the top plate comprises a plurality of bearing tracks configured to slidably interact with the friction-reducing elements.

* * * * *